United States Patent
Brar et al.

(10) Patent No.: US 11,974,903 B2
(45) Date of Patent: May 7, 2024

(54) REDUCED PRESSURE THERAPY SYSTEMS AND METHODS INCLUDING AN ANTENNA

(71) Applicant: Smith & Nephew, Inc., Memphis, TN (US)

(72) Inventors: Manveer Brar, San Diego, CA (US); William W. Gregory, Gainesville, FL (US); Felix Clarence Quintanar, Hull (GB)

(73) Assignee: Smith & Nephew, Inc., Memphis, TN (US)

( * ) Notice: Subject to any disclaimer, the term of this patent is extended or adjusted under 35 U.S.C. 154(b) by 766 days.

(21) Appl. No.: 16/491,542

(22) PCT Filed: Mar. 5, 2018

(86) PCT No.: PCT/US2018/020969
§ 371 (c)(1),
(2) Date: Sep. 5, 2019

(87) PCT Pub. No.: WO2018/165049
PCT Pub. Date: Sep. 13, 2018

(65) Prior Publication Data
US 2021/0030932 A1    Feb. 4, 2021

Related U.S. Application Data

(60) Provisional application No. 62/468,358, filed on Mar. 7, 2017.

(51) Int. Cl.
*A61F 13/05*    (2024.01)
*A61M 1/00*    (2006.01)
(Continued)

(52) U.S. Cl.
CPC ............ *A61F 13/05* (2024.01); *A61M 1/73* (2021.05); *H01Q 1/241* (2013.01); *H01Q 1/48* (2013.01);
(Continued)

(58) Field of Classification Search
CPC ............ A61M 1/90; A61M 2205/3331; A61M 2205/3592; H01Q 5/307; H01Q 1/241;
(Continued)

(56) References Cited

U.S. PATENT DOCUMENTS

| 695,270 A | 3/1902 | Beringer |
| 2,284,131 A | 5/1942 | Case |

(Continued)

FOREIGN PATENT DOCUMENTS

| CN | 1797418 A | 7/2006 |
| CN | 201921164 U | 8/2011 |

(Continued)

OTHER PUBLICATIONS

Analog Devices., "MT-095 Tutorial—EMI, RFI, and Shielding Concepts," Jan. 2009, 16 pages.

(Continued)

*Primary Examiner* — Benjamin J Klein
*Assistant Examiner* — Kate Elizabeth Strachan
(74) *Attorney, Agent, or Firm* — Knobbe, Martens, Olson & Bear, LLP

(57) ABSTRACT

Embodiments of negative pressure wound therapy systems and methods are disclosed. In some embodiments, an apparatus includes a housing enclosing a source of negative pressure and a controller configured to operate the source of negative pressure to provide negative pressure wound therapy to a wound. The housing can also include a communications controller configured to wirelessly transmit and receive data using a communications antenna positioned on (Continued)

an antenna board. The antenna board can be mounted to a communications board that include the communications controller. The antenna board can be electrically connected to the communications board via a single connector on the communications board. The antenna's ground plane can be positioned on the communications board.

20 Claims, 22 Drawing Sheets

(51) Int. Cl.
  *H01Q 1/24* (2006.01)
  *H01Q 1/48* (2006.01)
  *H01Q 5/307* (2015.01)
  *H01Q 9/04* (2006.01)

(52) U.S. Cl.
  CPC ........... *H01Q 5/307* (2015.01); *H01Q 9/0421* (2013.01); *A61M 1/915* (2021.05); *A61M 1/916* (2021.05); *A61M 1/962* (2021.05); *A61M 2205/3331* (2013.01); *A61M 2205/3592* (2013.01)

(58) Field of Classification Search
  CPC .... H01Q 1/48; H01Q 9/0421; A61F 13/00068
  See application file for complete search history.

(56) References Cited

U.S. PATENT DOCUMENTS

| | | | |
|---|---|---|---|
| 3,194,239 A | 7/1965 | Sullivan et al. | |
| 4,400,595 A | 8/1983 | Ahumada | |
| 4,832,299 A | 5/1989 | Gorton et al. | |
| 5,219,428 A | 6/1993 | Stern | |
| 5,473,536 A | 12/1995 | Wimmer | |
| 5,960,403 A | 9/1999 | Brown | |
| 6,055,506 A | 4/2000 | Frasca et al. | |
| 6,336,900 B1 | 1/2002 | Alleckson et al. | |
| 6,353,445 B1 | 3/2002 | Babula et al. | |
| 6,375,614 B1 | 4/2002 | Braun et al. | |
| 6,385,622 B2 | 5/2002 | Bouve et al. | |
| 6,406,426 B1 | 6/2002 | Reuss et al. | |
| 6,434,572 B2 | 8/2002 | Derzay et al. | |
| 6,460,041 B2 | 10/2002 | Lloyd | |
| 6,574,518 B1 | 6/2003 | Lounsberry et al. | |
| 6,640,145 B2 | 10/2003 | Hoffberg et al. | |
| 6,640,246 B1 | 10/2003 | Gary et al. | |
| 6,675,131 B2 | 1/2004 | Hahn | |
| 6,681,003 B2 | 1/2004 | Linder et al. | |
| 6,723,046 B2 | 4/2004 | Lichtenstein et al. | |
| 6,730,024 B2 | 5/2004 | Freyre et al. | |
| 6,747,556 B2 | 6/2004 | Medema et al. | |
| 6,779,024 B2 | 8/2004 | DeLahuerga | |
| 6,782,285 B2 | 8/2004 | Birkenbach et al. | |
| 6,856,825 B2 | 2/2005 | Hahn | |
| 6,868,528 B2 | 3/2005 | Roberts | |
| 6,871,211 B2 | 3/2005 | Labounty et al. | |
| 6,909,974 B2 | 6/2005 | Yung et al. | |
| 6,912,481 B2 | 6/2005 | Breunissen et al. | |
| 6,927,740 B2 | 8/2005 | Sergi | |
| 6,961,731 B2 | 11/2005 | Holbrook | |
| 7,004,915 B2 | 2/2006 | Boynton et al. | |
| 7,015,868 B2 * | 3/2006 | Puente Baliarde .... | H01Q 5/307 343/800 |
| 7,022,113 B2 | 4/2006 | Lockwood et al. | |
| 7,051,012 B2 | 5/2006 | Cole et al. | |
| 7,062,251 B2 | 6/2006 | Birkett et al. | |
| 7,066,883 B2 | 6/2006 | Schmidt et al. | |
| 7,103,578 B2 | 9/2006 | Beck et al. | |
| 7,108,683 B2 | 9/2006 | Zamierowski | |
| 7,120,488 B2 | 10/2006 | Nova et al. | |
| 7,133,869 B2 | 11/2006 | Bryan et al. | |
| 7,167,858 B2 | 1/2007 | Naeymi-Rad et al. | |
| 7,212,829 B1 | 5/2007 | Lau et al. | |
| 7,264,591 B2 | 9/2007 | Brown | |
| 7,300,418 B2 | 11/2007 | Zaleski | |
| 7,304,573 B2 | 12/2007 | Postma | |
| 7,311,665 B2 | 12/2007 | Hawthorne et al. | |
| 7,333,002 B2 | 2/2008 | Bixler et al. | |
| 7,353,179 B2 | 4/2008 | Ott et al. | |
| 7,384,267 B1 | 6/2008 | Franks et al. | |
| 7,384,403 B2 | 6/2008 | Sherman | |
| 7,430,598 B2 | 9/2008 | Raden et al. | |
| 7,430,608 B2 | 9/2008 | Noonan et al. | |
| 7,438,705 B2 | 10/2008 | Karpowicz et al. | |
| 7,451,002 B2 | 11/2008 | Choubey | |
| 7,457,804 B2 | 11/2008 | Uber et al. | |
| 7,460,872 B2 | 12/2008 | Millard et al. | |
| 7,492,278 B2 | 2/2009 | Zigmond et al. | |
| 7,534,240 B1 | 5/2009 | Johnson | |
| 7,598,855 B2 | 10/2009 | Scalisi et al. | |
| 7,608,066 B2 | 10/2009 | Vogel | |
| 7,627,334 B2 | 12/2009 | Cohen et al. | |
| 7,649,449 B2 | 1/2010 | Fenske et al. | |
| 7,671,733 B2 | 3/2010 | McNeal et al. | |
| 7,684,999 B2 | 3/2010 | Brown | |
| 7,734,764 B2 | 6/2010 | Weiner et al. | |
| 7,749,164 B2 | 7/2010 | Davis | |
| 7,758,555 B2 | 7/2010 | Kelch et al. | |
| 7,779,153 B2 | 8/2010 | Van Den Heuvel et al. | |
| 7,789,828 B2 | 9/2010 | Clapp | |
| 7,794,438 B2 | 9/2010 | Henley et al. | |
| 7,827,148 B2 | 11/2010 | Mori et al. | |
| 7,865,375 B2 | 1/2011 | Lancaster et al. | |
| 7,889,069 B2 | 2/2011 | Fifolt et al. | |
| 7,890,887 B1 | 2/2011 | Linardos et al. | |
| 7,912,823 B2 | 3/2011 | Ferrari et al. | |
| 7,925,603 B1 | 4/2011 | Laidig et al. | |
| 7,933,817 B2 | 4/2011 | Radl et al. | |
| 7,976,519 B2 | 7/2011 | Bubb et al. | |
| 7,981,098 B2 | 7/2011 | Boehringer et al. | |
| 7,988,850 B2 | 8/2011 | Roncadi et al. | |
| 8,015,443 B2 | 9/2011 | Adachi | |
| 8,015,972 B2 | 9/2011 | Pirzada | |
| 8,019,618 B2 | 9/2011 | Brown | |
| 8,036,925 B2 | 10/2011 | Choubey | |
| 8,054,950 B1 | 11/2011 | Hung et al. | |
| 8,069,057 B2 | 11/2011 | Choubey et al. | |
| 8,094,009 B2 | 1/2012 | Allen et al. | |
| 8,126,735 B2 | 2/2012 | Dicks et al. | |
| 8,130,095 B2 | 3/2012 | Allen et al. | |
| 8,131,472 B2 | 3/2012 | Chow et al. | |
| 8,180,750 B2 | 5/2012 | Wilmering et al. | |
| 8,190,445 B2 | 5/2012 | Kuth et al. | |
| 8,190,448 B2 | 5/2012 | Bajars et al. | |
| 8,228,188 B2 | 7/2012 | Key et al. | |
| 8,246,606 B2 | 8/2012 | Stevenson et al. | |
| 8,249,894 B2 | 8/2012 | Brown | |
| 8,255,241 B2 | 8/2012 | Cafer | |
| 8,260,630 B2 | 9/2012 | Brown | |
| 8,280,682 B2 | 10/2012 | Vock et al. | |
| 8,284,046 B2 | 10/2012 | Allen et al. | |
| 8,290,792 B2 | 10/2012 | Sekura | |
| 8,291,337 B2 | 10/2012 | Gannin et al. | |
| 8,306,496 B2 | 11/2012 | Shoji et al. | |
| 8,332,233 B2 | 12/2012 | Ott et al. | |
| 8,332,236 B2 | 12/2012 | Yurko et al. | |
| 8,334,768 B2 | 12/2012 | Eaton et al. | |
| 8,337,482 B2 | 12/2012 | Wood et al. | |
| 8,360,975 B1 | 1/2013 | Schwieterman et al. | |
| 8,400,295 B1 | 3/2013 | Khaira | |
| 8,422,377 B2 | 4/2013 | Weiner et al. | |
| 8,424,517 B2 | 4/2013 | Sutherland et al. | |
| 8,436,871 B2 | 5/2013 | Alberte | |
| 8,439,882 B2 | 5/2013 | Kelch | |
| 8,457,740 B2 | 6/2013 | Osche | |
| 8,480,641 B2 | 7/2013 | Jacobs | |
| 8,515,776 B2 | 8/2013 | Schoenberg | |
| 8,532,764 B2 | 9/2013 | Duke | |
| 8,540,688 B2 | 9/2013 | Eckstein et al. | |
| 8,545,483 B2 | 10/2013 | Schwabe et al. | |
| 8,554,195 B2 | 10/2013 | Rao | |

(56) References Cited

U.S. PATENT DOCUMENTS

| | | |
|---|---|---|
| 8,554,902 B2 | 10/2013 | Ebert et al. |
| 8,558,964 B2 | 10/2013 | Bedingfield |
| 8,560,082 B2 | 10/2013 | Wei |
| 8,577,694 B2 | 11/2013 | Kanaan |
| 8,595,553 B2 | 11/2013 | Goertler et al. |
| 8,600,777 B2 | 12/2013 | Schoenberg et al. |
| 8,626,342 B2 | 1/2014 | Williams et al. |
| 8,626,526 B2 | 1/2014 | Lemke et al. |
| 8,632,485 B2 | 1/2014 | Schlaeper et al. |
| 8,641,693 B2 | 2/2014 | Locke et al. |
| 8,659,420 B2 | 2/2014 | Salvat et al. |
| 8,676,597 B2 | 3/2014 | Buehler et al. |
| 8,686,919 B1 | 4/2014 | Sergi |
| 8,689,008 B2 | 4/2014 | Rangadass et al. |
| 8,694,600 B2 | 4/2014 | Gaines et al. |
| 8,706,537 B1 | 4/2014 | Young et al. |
| 8,725,528 B2 | 5/2014 | Locke et al. |
| 8,756,078 B2 | 6/2014 | Collins et al. |
| 8,757,485 B2 | 6/2014 | Drees et al. |
| 8,758,315 B2 | 6/2014 | Chen et al. |
| 8,768,441 B2 | 7/2014 | De Zwart et al. |
| 8,769,625 B2 | 7/2014 | Wang et al. |
| 8,781,847 B2 | 7/2014 | Simms et al. |
| 8,795,171 B2 | 8/2014 | Adamczyk |
| 8,795,244 B2 | 8/2014 | Randolph et al. |
| 8,838,136 B2 | 9/2014 | Carnes et al. |
| 8,840,660 B2 | 9/2014 | Weber |
| 8,862,393 B2 | 10/2014 | Zhou et al. |
| 8,868,794 B2 | 10/2014 | Masoud et al. |
| 8,874,035 B2 | 10/2014 | Sherman et al. |
| 8,887,100 B1 | 11/2014 | Cook et al. |
| 8,890,656 B2 | 11/2014 | Pendse |
| 8,897,198 B2 | 11/2014 | Gaines et al. |
| 8,902,278 B2 | 12/2014 | Pinter et al. |
| 8,905,959 B2 | 12/2014 | Basaglia |
| 8,909,595 B2 | 12/2014 | Gandy et al. |
| 8,912,897 B2 | 12/2014 | Carnes |
| 8,922,377 B2 | 12/2014 | Carnes |
| 8,945,073 B2 | 2/2015 | Croizat et al. |
| 8,947,237 B2 | 2/2015 | Margon et al. |
| 8,976,062 B2 | 3/2015 | Park et al. |
| 8,978,026 B2 | 3/2015 | Charlton et al. |
| 8,996,393 B2 | 3/2015 | Sobie |
| 9,047,648 B1 | 6/2015 | Lekutai et al. |
| 9,058,634 B2 | 6/2015 | Buan et al. |
| 9,081,885 B2 | 7/2015 | Bangera et al. |
| 9,087,141 B2 | 7/2015 | Huang et al. |
| 9,092,705 B2 | 7/2015 | Zhuang |
| 9,098,114 B2 | 8/2015 | Potter et al. |
| 9,105,006 B2 | 8/2015 | Williamson |
| 9,117,012 B2 | 8/2015 | Basaglia |
| 9,135,398 B2 | 9/2015 | Kaib et al. |
| 9,141,270 B1 | 9/2015 | Stuart et al. |
| 9,159,148 B2 | 10/2015 | Boyer et al. |
| 9,215,516 B2 | 12/2015 | Carnes et al. |
| 9,215,581 B2 | 12/2015 | Julian et al. |
| 9,230,420 B2 | 1/2016 | Lee et al. |
| 9,268,827 B2 | 2/2016 | Fernandez |
| 9,286,443 B2 | 3/2016 | Ford et al. |
| 9,323,893 B2 | 4/2016 | Berry et al. |
| 9,332,363 B2 | 5/2016 | Jain et al. |
| 9,338,819 B2 | 5/2016 | Meng et al. |
| 9,424,020 B2 | 8/2016 | Borges et al. |
| 9,427,159 B2 | 8/2016 | Chang |
| 9,436,645 B2 | 9/2016 | Al-Ali et al. |
| 9,436,800 B2 | 9/2016 | Forrester |
| 9,439,584 B1 | 9/2016 | De Vries et al. |
| 9,460,431 B2 | 10/2016 | Curry |
| 9,474,679 B2 | 10/2016 | Locke et al. |
| 9,483,614 B2 | 11/2016 | Ash et al. |
| 9,539,373 B2 | 1/2017 | Jones et al. |
| 9,545,466 B2 | 1/2017 | Locke et al. |
| 9,558,331 B2 | 1/2017 | Orona et al. |
| 9,585,565 B2 | 3/2017 | Carnes |
| 9,589,247 B2 | 3/2017 | Bolene et al. |
| 9,602,952 B2 | 3/2017 | Kang et al. |
| 9,629,986 B2 | 4/2017 | Patel et al. |
| 9,658,066 B2 | 5/2017 | Yuen et al. |
| 9,662,438 B2 | 5/2017 | Kamen et al. |
| 9,687,618 B2 | 6/2017 | Steinhauer et al. |
| 9,693,691 B2 | 7/2017 | Johnson |
| 9,700,462 B2 | 7/2017 | DeBusk et al. |
| 9,716,757 B2 | 7/2017 | Fernandes |
| 9,740,825 B2 | 8/2017 | Sansale et al. |
| 9,741,084 B2 | 8/2017 | Holmes et al. |
| 9,787,842 B1 | 10/2017 | Brooksby et al. |
| 9,792,660 B2 | 10/2017 | Cannon et al. |
| 9,817,948 B2 | 11/2017 | Swank |
| 9,818,164 B2 | 11/2017 | Nolte et al. |
| 9,838,645 B2 | 12/2017 | Hyde et al. |
| 9,878,081 B2 | 1/2018 | Leiendecker et al. |
| 9,905,123 B2 | 2/2018 | Lawhorn |
| 9,928,478 B2 | 3/2018 | Ragusky et al. |
| 9,974,492 B1 | 5/2018 | Dicks et al. |
| 9,990,466 B2 | 6/2018 | DeBusk et al. |
| 9,996,681 B2 | 6/2018 | Suarez et al. |
| 10,049,346 B2 | 8/2018 | Jensen et al. |
| 10,061,894 B2 | 8/2018 | Sethumadhavan et al. |
| 10,064,551 B2 | 9/2018 | Cosentino et al. |
| 10,095,649 B2 | 10/2018 | Joshua et al. |
| 10,127,357 B2 | 11/2018 | Whiting et al. |
| 10,152,575 B2 | 12/2018 | Sexton et al. |
| 10,173,008 B2 | 1/2019 | Simpson et al. |
| 10,185,834 B2 | 1/2019 | Adam et al. |
| 10,207,031 B2 | 2/2019 | Toth |
| 10,300,180 B1 | 5/2019 | Quisenberry et al. |
| 10,328,188 B2 | 6/2019 | Deutsch et al. |
| 10,556,045 B2 | 2/2020 | Carr et al. |
| 2002/0087360 A1 | 7/2002 | Pettit |
| 2002/0128804 A1 | 9/2002 | Geva |
| 2002/0128869 A1 | 9/2002 | Kuth |
| 2002/0135336 A1 | 9/2002 | Zhou et al. |
| 2002/0177757 A1 | 11/2002 | Britton |
| 2002/0184055 A1 | 12/2002 | Naghavi et al. |
| 2003/0009244 A1 | 1/2003 | Engleson et al. |
| 2003/0018736 A1 | 1/2003 | Christ et al. |
| 2003/0105649 A1 | 6/2003 | Sheiner et al. |
| 2003/0182158 A1 | 9/2003 | Son |
| 2003/0221687 A1 | 12/2003 | Kaigler |
| 2003/0229518 A1 | 12/2003 | Abraham-Fuchs et al. |
| 2004/0006492 A1 | 1/2004 | Watanabe |
| 2004/0019464 A1 | 1/2004 | Martucci et al. |
| 2004/0054775 A1 | 3/2004 | Poliac et al. |
| 2004/0078223 A1 | 4/2004 | Sacco et al. |
| 2004/0143458 A1 | 7/2004 | Pulkkinen et al. |
| 2004/0167802 A1 | 8/2004 | Takada et al. |
| 2004/0167804 A1 | 8/2004 | Simpson et al. |
| 2004/0172301 A1 | 9/2004 | Mihai et al. |
| 2004/0181433 A1 | 9/2004 | Blair |
| 2004/0193449 A1 | 9/2004 | Wildman et al. |
| 2004/0204962 A1 | 10/2004 | Howser et al. |
| 2005/0033124 A1 | 2/2005 | Kelly et al. |
| 2005/0055225 A1 | 3/2005 | Mehl |
| 2005/0055242 A1 | 3/2005 | Bello et al. |
| 2005/0055244 A1 | 3/2005 | Mullan et al. |
| 2005/0060211 A1 | 3/2005 | Xiao et al. |
| 2005/0065817 A1 | 3/2005 | Mihai et al. |
| 2005/0097200 A1 | 5/2005 | Denning et al. |
| 2005/0102167 A1 | 5/2005 | Kapoor |
| 2005/0108046 A1 | 5/2005 | Craft |
| 2005/0108057 A1 | 5/2005 | Cohen et al. |
| 2005/0114176 A1 | 5/2005 | Dominick et al. |
| 2005/0119914 A1 | 6/2005 | Batch |
| 2005/0222873 A1 | 10/2005 | Nephin et al. |
| 2005/0240111 A1 | 10/2005 | Chung |
| 2005/0283382 A1 | 12/2005 | Donoghue et al. |
| 2006/0004604 A1 | 1/2006 | White |
| 2006/0064323 A1 | 3/2006 | Alleckson et al. |
| 2006/0085393 A1 | 4/2006 | Modesitt |
| 2006/0089539 A1 | 4/2006 | Miodownik et al. |
| 2006/0095853 A1 | 5/2006 | Amyot et al. |
| 2006/0155584 A1 | 7/2006 | Aggarwal |
| 2006/0161460 A1 | 7/2006 | Smitherman et al. |
| 2006/0190130 A1 | 8/2006 | Fedor et al. |

(56) References Cited

U.S. PATENT DOCUMENTS

| | | |
|---|---|---|
| 2006/0195843 A1 | 8/2006 | Hall |
| 2006/0224051 A1 | 10/2006 | Teller et al. |
| 2006/0246922 A1 | 11/2006 | Gasbarro et al. |
| 2007/0136099 A1 | 6/2007 | Neligh et al. |
| 2007/0139279 A1 | 6/2007 | Kakinoki et al. |
| 2007/0156456 A1 | 7/2007 | Mcgillin et al. |
| 2007/0197881 A1 | 8/2007 | Wolf et al. |
| 2007/0219826 A1 | 9/2007 | Brodsky et al. |
| 2007/0255116 A1 | 11/2007 | Mehta et al. |
| 2007/0271298 A1 | 11/2007 | Juang et al. |
| 2008/0009681 A1 | 1/2008 | Al Hussiny |
| 2008/0041401 A1 | 2/2008 | Casola et al. |
| 2008/0086357 A1 | 4/2008 | Choubey et al. |
| 2008/0091659 A1 | 4/2008 | McFaul |
| 2008/0119705 A1 | 5/2008 | Patel et al. |
| 2008/0126126 A1 | 5/2008 | Ballai |
| 2008/0140160 A1 | 6/2008 | Goetz et al. |
| 2008/0167534 A1 | 7/2008 | Young et al. |
| 2008/0177579 A1 | 7/2008 | Dehaan |
| 2008/0221396 A1 | 9/2008 | Garces et al. |
| 2008/0242945 A1 | 10/2008 | Gugliotti et al. |
| 2008/0312953 A1 | 12/2008 | Claus |
| 2009/0037220 A1 | 2/2009 | Chambers et al. |
| 2009/0048492 A1 | 2/2009 | Rantala et al. |
| 2009/0048865 A1 | 2/2009 | Breazeale, Jr. |
| 2009/0066604 A1 | 3/2009 | Fan |
| 2009/0097623 A1 | 4/2009 | Bharadwaj |
| 2009/0099866 A1 | 4/2009 | Newman |
| 2009/0099867 A1 | 4/2009 | Newman |
| 2009/0105646 A1 | 4/2009 | Hendrixson et al. |
| 2009/0115663 A1 | 5/2009 | Brown et al. |
| 2009/0118591 A1 | 5/2009 | Kim et al. |
| 2009/0125331 A1 | 5/2009 | Pamsgaard et al. |
| 2009/0136909 A1 | 5/2009 | Asukai et al. |
| 2009/0144091 A1 | 6/2009 | Rago |
| 2009/0157429 A1 | 6/2009 | Lee et al. |
| 2009/0163774 A1 | 6/2009 | Thatha et al. |
| 2009/0171166 A1 | 7/2009 | Amundson et al. |
| 2009/0177495 A1 | 7/2009 | Abousy et al. |
| 2009/0187424 A1 | 7/2009 | Grabowski |
| 2009/0204434 A1 | 8/2009 | Breazeale, Jr. |
| 2009/0204435 A1 | 8/2009 | Gale |
| 2009/0205042 A1 | 8/2009 | Zhou et al. |
| 2009/0224889 A1 | 9/2009 | Aggarwal et al. |
| 2009/0256762 A1 | 10/2009 | Weakley |
| 2009/0270833 A1 | 10/2009 | DeBelser et al. |
| 2009/0281822 A1 | 11/2009 | Warner et al. |
| 2009/0281830 A1 | 11/2009 | Mcnames et al. |
| 2009/0281867 A1 | 11/2009 | Sievenpiper et al. |
| 2009/0326339 A1 | 12/2009 | Horvitz |
| 2009/0327102 A1 | 12/2009 | Maniar et al. |
| 2010/0001838 A1 | 1/2010 | Miodownik et al. |
| 2010/0017471 A1 | 1/2010 | Brown et al. |
| 2010/0022848 A1 | 1/2010 | Lee et al. |
| 2010/0022990 A1 | 1/2010 | Karpowicz et al. |
| 2010/0030302 A1 | 2/2010 | Blowers et al. |
| 2010/0036333 A1 | 2/2010 | Schenk, III et al. |
| 2010/0090004 A1 | 4/2010 | Sands et al. |
| 2010/0106528 A1 | 4/2010 | Brackett et al. |
| 2010/0113908 A1 | 5/2010 | Vargas et al. |
| 2010/0145161 A1 | 6/2010 | Niyato et al. |
| 2010/0222645 A1 | 9/2010 | Nadler et al. |
| 2010/0234708 A1 | 9/2010 | Buck et al. |
| 2010/0255876 A1 | 10/2010 | Jordan et al. |
| 2011/0004188 A1 | 1/2011 | Shekalim |
| 2011/0015593 A1 | 1/2011 | Svedman et al. |
| 2011/0066110 A1 | 3/2011 | Fathallah et al. |
| 2011/0071844 A1 | 3/2011 | Cannon et al. |
| 2011/0073107 A1 | 3/2011 | Rodman et al. |
| 2011/0077605 A1 | 3/2011 | Karpowicz et al. |
| 2011/0106561 A1 | 5/2011 | Eaton, Jr. et al. |
| 2011/0122045 A1 | 5/2011 | Seo et al. |
| 2011/0137759 A1 | 6/2011 | Wellington et al. |
| 2011/0145018 A1 | 6/2011 | Fotsch et al. |
| 2011/0173028 A1 | 7/2011 | Bond |
| 2011/0184754 A1 | 7/2011 | Park et al. |
| 2011/0225008 A1 | 9/2011 | Elkouh et al. |
| 2011/0246219 A1 | 10/2011 | Smith et al. |
| 2011/0275353 A1 | 11/2011 | Liu |
| 2011/0288878 A1 | 11/2011 | Blair |
| 2012/0029312 A1 | 2/2012 | Beaudry et al. |
| 2012/0029313 A1 | 2/2012 | Burdett et al. |
| 2012/0032819 A1 | 2/2012 | Chae et al. |
| 2012/0035427 A1 | 2/2012 | Friedman et al. |
| 2012/0077605 A1 | 3/2012 | Nakagaito et al. |
| 2012/0081225 A1 | 4/2012 | Waugh et al. |
| 2012/0089369 A1 | 4/2012 | Abuzeni et al. |
| 2012/0109034 A1 | 5/2012 | Locke et al. |
| 2012/0123323 A1 | 5/2012 | Kagan et al. |
| 2012/0123796 A1 | 5/2012 | Mcfaul |
| 2012/0157889 A1 | 6/2012 | Tanis et al. |
| 2012/0181405 A1 | 7/2012 | Zlatic et al. |
| 2012/0182143 A1 | 7/2012 | Gaines et al. |
| 2012/0191475 A1 | 7/2012 | Pandey |
| 2012/0212455 A1 | 8/2012 | Kloeffel |
| 2012/0215455 A1 | 8/2012 | Patil et al. |
| 2012/0259651 A1 | 10/2012 | Mallon et al. |
| 2012/0271256 A1 | 10/2012 | Locke et al. |
| 2012/0290217 A1 | 11/2012 | Shoval et al. |
| 2012/0293322 A1 | 11/2012 | Ray et al. |
| 2012/0295566 A1 | 11/2012 | Collins et al. |
| 2012/0310205 A1 | 12/2012 | Lee et al. |
| 2013/0018355 A1 | 1/2013 | Brand et al. |
| 2013/0023719 A1 | 1/2013 | Bennett |
| 2013/0035615 A1 | 2/2013 | Hsieh |
| 2013/0045764 A1 | 2/2013 | Vik et al. |
| 2013/0073303 A1 | 3/2013 | Hsu |
| 2013/0076528 A1 | 3/2013 | Boettner et al. |
| 2013/0087609 A1 | 4/2013 | Nichol et al. |
| 2013/0090949 A1 | 4/2013 | Tibebu |
| 2013/0103419 A1 | 4/2013 | Beaudry |
| 2013/0124227 A1 | 5/2013 | Ellis |
| 2013/0132855 A1 | 5/2013 | Manicka et al. |
| 2013/0150686 A1 | 6/2013 | Fronterhouse et al. |
| 2013/0150698 A1 | 6/2013 | Hsu et al. |
| 2013/0151274 A1 | 6/2013 | Bage et al. |
| 2013/0157571 A1 | 6/2013 | Wondka et al. |
| 2013/0159456 A1 | 6/2013 | Daoud et al. |
| 2013/0160082 A1 | 6/2013 | Miller |
| 2013/0170884 A1 | 7/2013 | Chou |
| 2013/0181874 A1 | 7/2013 | Park et al. |
| 2013/0186405 A1 | 7/2013 | Krzyzanowski et al. |
| 2013/0190903 A1 | 7/2013 | Balakrishnan et al. |
| 2013/0191513 A1 | 7/2013 | Kamen et al. |
| 2013/0196703 A1 | 8/2013 | Masoud et al. |
| 2013/0204106 A1 | 8/2013 | Bennett |
| 2013/0211206 A1 | 8/2013 | Sands et al. |
| 2013/0211854 A1 | 8/2013 | Wagstaff |
| 2013/0212168 A1 | 8/2013 | Bonasera et al. |
| 2013/0214925 A1 | 8/2013 | Weiss |
| 2013/0218053 A1 | 8/2013 | Kaiser et al. |
| 2013/0226607 A1 | 8/2013 | Woody et al. |
| 2013/0227128 A1 | 8/2013 | Wagstaff |
| 2013/0231596 A1 | 9/2013 | Hornbach et al. |
| 2013/0245387 A1 | 9/2013 | Patel |
| 2013/0253952 A1 | 9/2013 | Burke et al. |
| 2013/0255681 A1 | 10/2013 | Batch et al. |
| 2013/0267919 A1 | 10/2013 | Caso et al. |
| 2013/0268283 A1 | 10/2013 | Vann et al. |
| 2013/0271278 A1* | 10/2013 | Duesterhoft ............ A61B 5/445 340/539.12 |
| 2013/0271556 A1 | 10/2013 | Ross et al. |
| 2013/0274629 A1* | 10/2013 | Duesterhoft ............ G16Z 99/00 600/573 |
| 2013/0282395 A1 | 10/2013 | Rustgi et al. |
| 2013/0285837 A1 | 10/2013 | Uchida |
| 2013/0297350 A1 | 11/2013 | Gross et al. |
| 2013/0304489 A1 | 11/2013 | Miller |
| 2013/0310726 A1 | 11/2013 | Miller et al. |
| 2013/0317753 A1 | 11/2013 | Kamen et al. |
| 2013/0325508 A1 | 12/2013 | Johnson et al. |
| 2013/0331748 A1 | 12/2013 | Wright et al. |
| 2013/0332197 A1 | 12/2013 | Hinkel |
| 2013/0335233 A1 | 12/2013 | Kamar et al. |

(56) References Cited

U.S. PATENT DOCUMENTS

| | | |
|---|---|---|
| 2013/0339049 A1 | 12/2013 | Blumberg, Jr. et al. |
| 2013/0345524 A1 | 12/2013 | Meyer et al. |
| 2014/0002234 A1 | 1/2014 | Alwan |
| 2014/0005618 A1* | 1/2014 | Locke .................. A61M 1/732 604/319 |
| 2014/0028464 A1 | 1/2014 | Garibaldi |
| 2014/0031884 A1 | 1/2014 | Elghazzawi |
| 2014/0032231 A1 | 1/2014 | Semen et al. |
| 2014/0058714 A1 | 2/2014 | Boyer |
| 2014/0087762 A1 | 3/2014 | Galvin et al. |
| 2014/0108033 A1 | 4/2014 | Akbay et al. |
| 2014/0108034 A1 | 4/2014 | Akbay et al. |
| 2014/0108035 A1 | 4/2014 | Akbay et al. |
| 2014/0129250 A1 | 5/2014 | Daniel et al. |
| 2014/0148138 A1 | 5/2014 | Chou |
| 2014/0163462 A1 | 6/2014 | Qi et al. |
| 2014/0171753 A1 | 6/2014 | Montejo et al. |
| 2014/0187888 A1 | 7/2014 | Hatziantoniou |
| 2014/0207090 A1 | 7/2014 | Jian |
| 2014/0222446 A1 | 8/2014 | Ash et al. |
| 2014/0235975 A1 | 8/2014 | Carnes |
| 2014/0244285 A1 | 8/2014 | Hinkle et al. |
| 2014/0244301 A1 | 8/2014 | Lee et al. |
| 2014/0244307 A1 | 8/2014 | Shutko et al. |
| 2014/0266713 A1 | 9/2014 | Sehgal et al. |
| 2014/0275876 A1 | 9/2014 | Hansen et al. |
| 2014/0278502 A1 | 9/2014 | Laskin |
| 2014/0280882 A1 | 9/2014 | Lacerte et al. |
| 2014/0297299 A1 | 10/2014 | Lester, IV |
| 2014/0316819 A1 | 10/2014 | Dunsirn et al. |
| 2014/0336597 A1 | 11/2014 | Coulthard et al. |
| 2014/0350966 A1 | 11/2014 | Khatana et al. |
| 2014/0366878 A1 | 12/2014 | Baron |
| 2014/0372147 A1 | 12/2014 | White |
| 2014/0372522 A1 | 12/2014 | Orona et al. |
| 2014/0375470 A1 | 12/2014 | Malveaux |
| 2014/0378895 A1 | 12/2014 | Barack |
| 2015/0012290 A1 | 1/2015 | Inciardi et al. |
| 2015/0019237 A1 | 1/2015 | Doyle et al. |
| 2015/0019257 A1 | 1/2015 | Doyle et al. |
| 2015/0025482 A1 | 1/2015 | Begin et al. |
| 2015/0025486 A1 | 1/2015 | Hu et al. |
| 2015/0046137 A1 | 2/2015 | Zeilinger |
| 2015/0066531 A1 | 3/2015 | Jacobson et al. |
| 2015/0072613 A1 | 3/2015 | Swanson |
| 2015/0094830 A1 | 4/2015 | Lipoma et al. |
| 2015/0095056 A1 | 4/2015 | Ryan et al. |
| 2015/0095059 A1 | 4/2015 | Yegge et al. |
| 2015/0095066 A1 | 4/2015 | Ryan et al. |
| 2015/0095068 A1 | 4/2015 | Ryan et al. |
| 2015/0100340 A1 | 4/2015 | Folsom et al. |
| 2015/0112707 A1 | 4/2015 | Manice et al. |
| 2015/0118662 A1 | 4/2015 | Ellison et al. |
| 2015/0119652 A1 | 4/2015 | Hyde et al. |
| 2015/0120318 A1 | 4/2015 | Toyama |
| 2015/0143300 A1 | 5/2015 | Zhang et al. |
| 2015/0164323 A1 | 6/2015 | Holtzclaw |
| 2015/0164376 A1 | 6/2015 | Huang |
| 2015/0186615 A1 | 7/2015 | Armor et al. |
| 2015/0189001 A1 | 7/2015 | Lee et al. |
| 2015/0227716 A1 | 8/2015 | Ryan et al. |
| 2015/0227717 A1 | 8/2015 | Ryan et al. |
| 2015/0234557 A1 | 8/2015 | Dorn |
| 2015/0234995 A1 | 8/2015 | Casady et al. |
| 2015/0242578 A1 | 8/2015 | Siemon |
| 2015/0242583 A1 | 8/2015 | Edson |
| 2015/0254403 A1 | 9/2015 | Laperna |
| 2015/0257643 A1 | 9/2015 | Watson et al. |
| 2015/0261920 A1 | 9/2015 | Blick |
| 2015/0269323 A1 | 9/2015 | Ginsburg |
| 2015/0286970 A1 | 10/2015 | Dickerson et al. |
| 2015/0290441 A1 | 10/2015 | Locke et al. |
| 2015/0304478 A1 | 10/2015 | Kim et al. |
| 2015/0310182 A1 | 10/2015 | Henze et al. |
| 2015/0324943 A1 | 11/2015 | Han et al. |
| 2015/0339445 A1 | 11/2015 | Gruby et al. |
| 2015/0363058 A1 | 12/2015 | Chung et al. |
| 2015/0370984 A1 | 12/2015 | Russell et al. |
| 2015/0370997 A1 | 12/2015 | Krongrad et al. |
| 2015/0379441 A1 | 12/2015 | Syed et al. |
| 2016/0004824 A1 | 1/2016 | Stanton et al. |
| 2016/0018963 A1 | 1/2016 | Robbins et al. |
| 2016/0036127 A1 | 2/2016 | Desclos et al. |
| 2016/0042154 A1 | 2/2016 | Goldberg et al. |
| 2016/0044141 A1 | 2/2016 | Pfützenreuter et al. |
| 2016/0055310 A1 | 2/2016 | Bentley et al. |
| 2016/0058286 A1 | 3/2016 | Joshua et al. |
| 2016/0063210 A1 | 3/2016 | Bardi et al. |
| 2016/0066864 A1 | 3/2016 | Frieder et al. |
| 2016/0080365 A1 | 3/2016 | Baker et al. |
| 2016/0085415 A1 | 3/2016 | Humphrys et al. |
| 2016/0098524 A1 | 4/2016 | Himmelstein |
| 2016/0110507 A1 | 4/2016 | Abbo |
| 2016/0128571 A1 | 5/2016 | Adler |
| 2016/0129186 A1 | 5/2016 | Douglas et al. |
| 2016/0135752 A1 | 5/2016 | Beaumont |
| 2016/0142443 A1 | 5/2016 | Ting et al. |
| 2016/0151015 A1 | 6/2016 | Condurso et al. |
| 2016/0154936 A1 | 6/2016 | Kalathil |
| 2016/0154943 A1 | 6/2016 | Cho et al. |
| 2016/0171866 A1 | 6/2016 | Dupasquier et al. |
| 2016/0180031 A1 | 6/2016 | Slater |
| 2016/0184497 A1 | 6/2016 | Phillips et al. |
| 2016/0196399 A1 | 7/2016 | Bonhomme |
| 2016/0199561 A1* | 7/2016 | Dacey, Jr. .............. B01D 69/12 210/489 |
| 2016/0203275 A1 | 7/2016 | Benjamin et al. |
| 2016/0203283 A1 | 7/2016 | Baruah et al. |
| 2016/0209837 A1 | 7/2016 | Kim |
| 2016/0212577 A1 | 7/2016 | Dor et al. |
| 2016/0217433 A1 | 7/2016 | Walton et al. |
| 2016/0246943 A1 | 8/2016 | Lake et al. |
| 2016/0260035 A1 | 9/2016 | Crooks et al. |
| 2016/0287189 A1 | 10/2016 | Modai et al. |
| 2016/0308969 A1 | 10/2016 | Aihara et al. |
| 2016/0321404 A1 | 11/2016 | Ginsburg |
| 2016/0321422 A1 | 11/2016 | Albright |
| 2017/0007494 A1 | 1/2017 | Rock et al. |
| 2017/0014028 A1 | 1/2017 | Clear, Jr. |
| 2017/0017765 A1 | 1/2017 | Yegge et al. |
| 2017/0021172 A1* | 1/2017 | Perez ................. A61N 1/37211 |
| 2017/0032648 A1 | 2/2017 | Mcclain et al. |
| 2017/0046503 A1 | 2/2017 | Cho et al. |
| 2017/0053073 A1 | 2/2017 | Allen et al. |
| 2017/0055205 A1 | 2/2017 | Morris et al. |
| 2017/0068781 A1 | 3/2017 | Zasowski et al. |
| 2017/0074717 A1 | 3/2017 | Pilkington et al. |
| 2017/0078396 A1 | 3/2017 | Haas et al. |
| 2017/0085000 A1* | 3/2017 | Girard ...................... H01Q 1/48 |
| 2017/0116373 A1 | 4/2017 | Ginsburg et al. |
| 2017/0140120 A1 | 5/2017 | Thrower |
| 2017/0150939 A1 | 6/2017 | Shah |
| 2017/0193181 A1 | 7/2017 | Carter et al. |
| 2017/0212995 A1 | 7/2017 | Ingmanson |
| 2017/0220755 A1* | 8/2017 | Fowler ................. G06Q 10/087 |
| 2017/0244818 A1* | 8/2017 | Kim ...................... H01Q 5/335 |
| 2017/0257682 A1 | 9/2017 | Shtalryd |
| 2017/0270533 A1 | 9/2017 | Barton et al. |
| 2017/0273116 A1 | 9/2017 | Elghazzawi |
| 2017/0327371 A1 | 11/2017 | Bai et al. |
| 2017/0372010 A1 | 12/2017 | Doherty et al. |
| 2018/0004908 A1 | 1/2018 | Barrus et al. |
| 2018/0052454 A1 | 2/2018 | Magno et al. |
| 2018/0121629 A1 | 5/2018 | Dyer et al. |
| 2018/0139572 A1 | 5/2018 | Hansen |
| 2018/0144817 A1 | 5/2018 | Lofgren et al. |
| 2018/0158545 A1 | 6/2018 | Blomquist |
| 2018/0181714 A1 | 6/2018 | Pillarisetty et al. |
| 2018/0233016 A1 | 8/2018 | Daniel et al. |
| 2018/0233221 A1 | 8/2018 | Blomquist |
| 2018/0279880 A1 | 10/2018 | Bacchi |
| 2018/0286502 A1 | 10/2018 | Lane et al. |
| 2018/0308569 A1 | 10/2018 | Luellen |
| 2018/0308573 A1 | 10/2018 | Hochrein et al. |

(56) References Cited

U.S. PATENT DOCUMENTS

| | | | |
|---|---|---|---|
| 2018/0315492 A1 | 11/2018 | Bishop et al. | |
| 2018/0318476 A1 | 11/2018 | Askem et al. | |
| 2018/0322944 A1 | 11/2018 | Valdizan | |
| 2020/0104998 A1* | 4/2020 | Dacosta | A61B 5/445 |
| 2020/0121833 A9 | 4/2020 | Askem et al. | |

FOREIGN PATENT DOCUMENTS

| | | | |
|---|---|---|---|
| CN | 102805894 A | 12/2012 | |
| CN | 102961815 A | 3/2013 | |
| CN | 203707314 U | 7/2014 | |
| CN | 104124510 A | 10/2014 | |
| CN | 104702683 A | 6/2015 | |
| CN | 104721008 A | 6/2015 | |
| CN | 104721892 A | 6/2015 | |
| CN | 104795629 A | 7/2015 | |
| CN | 105514587 A | 4/2016 | |
| CN | 105514603 A * | 4/2016 | H01Q 1/243 |
| DE | 102009039336 A1 | 3/2011 | |
| DE | 102010036405 A1 | 1/2012 | |
| EP | 0322515 A2 | 7/1989 | |
| EP | 1079463 A2 | 2/2001 | |
| EP | 0566381 B1 | 7/2002 | |
| EP | 1231965 A2 | 8/2002 | |
| EP | 1291802 A2 | 3/2003 | |
| EP | 0814864 B1 | 12/2003 | |
| EP | 1407624 A2 | 4/2004 | |
| EP | 1011420 B1 | 12/2004 | |
| EP | 1495713 A1 | 1/2005 | |
| EP | 1524619 A2 | 4/2005 | |
| EP | 1540557 A2 | 6/2005 | |
| EP | 1579367 A2 | 9/2005 | |
| EP | 1587017 A2 | 10/2005 | |
| EP | 1684146 A2 | 7/2006 | |
| EP | 1788503 A2 | 5/2007 | |
| EP | 1839244 A1 | 10/2007 | |
| EP | 1839615 A1 | 10/2007 | |
| EP | 1857950 A2 | 11/2007 | |
| EP | 1870068 A1 | 12/2007 | |
| EP | 1904964 A1 | 4/2008 | |
| EP | 1934852 A1 | 6/2008 | |
| EP | 1975828 A2 | 10/2008 | |
| EP | 1993435 A2 | 11/2008 | |
| EP | 2038786 A2 | 3/2009 | |
| EP | 2040604 A2 | 4/2009 | |
| EP | 2092470 A2 | 8/2009 | |
| EP | 2146297 A1 | 1/2010 | |
| EP | 2172859 A1 | 4/2010 | |
| EP | 2214552 A1 | 8/2010 | |
| EP | 2218478 A1 | 8/2010 | |
| EP | 1404213 B1 | 3/2011 | |
| EP | 1247229 B1 | 4/2011 | |
| EP | 1406540 B1 | 6/2011 | |
| EP | 1812094 B1 | 8/2011 | |
| EP | 2384472 A1 | 11/2011 | |
| EP | 2226002 B1 | 1/2012 | |
| EP | 1610494 B1 | 3/2012 | |
| EP | 1248660 B1 | 4/2012 | |
| EP | 2023800 B1 | 4/2012 | |
| EP | 2451513 A1 | 5/2012 | |
| EP | 1248661 B1 | 8/2012 | |
| EP | 2488977 A1 | 8/2012 | |
| EP | 2562665 A2 | 2/2013 | |
| EP | 2619723 A2 | 7/2013 | |
| EP | 1881784 B1 | 10/2013 | |
| EP | 2664194 A2 | 11/2013 | |
| EP | 2743850 A2 | 6/2014 | |
| EP | 2745204 A1 | 6/2014 | |
| EP | 2841895 A1 | 3/2015 | |
| EP | 2850771 A1 | 3/2015 | |
| EP | 2876567 A1 | 5/2015 | |
| EP | 2891999 A2 | 7/2015 | |
| EP | 2894581 A1 | 7/2015 | |
| EP | 2906101 A2 | 8/2015 | |
| EP | 2945084 A1 | 11/2015 | |
| EP | 2962266 A1 | 1/2016 | |
| EP | 2968829 A1 | 1/2016 | |
| EP | 2973089 A1 | 1/2016 | |
| EP | 3000082 A1 | 3/2016 | |
| EP | 3010398 A1 | 4/2016 | |
| EP | 3054389 A2 | 8/2016 | |
| EP | 3070628 A1 | 9/2016 | |
| EP | 3078010 A1 | 10/2016 | |
| EP | 3096113 A1 | 11/2016 | |
| EP | 2563437 B1 | 3/2017 | |
| EP | 2773393 B1 | 3/2017 | |
| EP | 3134854 A1 | 3/2017 | |
| EP | 3027242 B1 | 4/2017 | |
| EP | 2556650 B1 | 5/2017 | |
| EP | 3209358 A1 | 8/2017 | |
| EP | 3041571 B1 | 9/2017 | |
| EP | 2856767 B1 | 11/2017 | |
| EP | 3252635 A1 | 12/2017 | |
| EP | 2320971 B1 | 5/2018 | |
| EP | 2335173 B1 | 5/2018 | |
| EP | 3100188 B1 | 6/2018 | |
| EP | 3330973 A1 | 6/2018 | |
| EP | 3352174 A1 | 7/2018 | |
| EP | 2440112 B1 | 10/2018 | |
| EP | 3400549 A1 | 11/2018 | |
| EP | 2992500 B1 | 12/2018 | |
| EP | 2597584 B1 | 1/2019 | |
| EP | 3219340 B1 | 1/2019 | |
| EP | 2890456 B1 | 2/2019 | |
| EP | 3377130 B1 | 4/2019 | |
| EP | 2881875 B1 | 5/2019 | |
| EP | 2866851 B1 | 9/2019 | |
| GB | 2409951 A | 7/2005 | |
| GB | 2436160 A | 9/2007 | |
| GB | 2449400 A | 11/2008 | |
| GB | 2456708 A | 7/2009 | |
| GB | 2423178 B | 5/2010 | |
| GB | 2475091 A | 5/2011 | |
| GB | 2488904 A | 9/2012 | |
| GB | 2446923 B | 5/2013 | |
| GB | 2499986 A | 9/2013 | |
| GB | 2491946 B | 8/2014 | |
| GB | 2499873 B | 5/2016 | |
| GB | 2533910 A | 7/2016 | |
| GB | 2541286 A | 2/2017 | |
| GB | 2550576 B | 6/2018 | |
| JP | 2009248783 A | 10/2009 | |
| WO | WO-9627163 A1 | 9/1996 | |
| WO | WO-9744745 A1 | 11/1997 | |
| WO | WO-9924927 A1 | 5/1999 | |
| WO | WO-9963886 A1 | 12/1999 | |
| WO | WO-0032088 A1 | 6/2000 | |
| WO | WO-0060522 A2 | 10/2000 | |
| WO | WO-0133457 A1 | 5/2001 | |
| WO | WO-0181829 A1 | 11/2001 | |
| WO | WO-0217075 A2 | 2/2002 | |
| WO | WO-0233577 A1 | 4/2002 | |
| WO | WO-02078594 A2 | 10/2002 | |
| WO | WO-02101713 A1 | 12/2002 | |
| WO | WO-03054668 A2 | 7/2003 | |
| WO | WO-03094090 A2 | 11/2003 | |
| WO | WO-2004057514 A2 | 7/2004 | |
| WO | WO-2004074457 A2 | 9/2004 | |
| WO | WO-2005022349 A2 | 3/2005 | |
| WO | WO-2005031632 A2 | 4/2005 | |
| WO | WO-2005036447 A2 | 4/2005 | |
| WO | WO-2005045461 A2 | 5/2005 | |
| WO | WO-2005053793 A1 | 6/2005 | |
| WO | WO-2005057466 A2 | 6/2005 | |
| WO | WO-2005083619 A2 | 9/2005 | |
| WO | WO-2005101282 A2 | 10/2005 | |
| WO | WO-2005109297 A2 | 11/2005 | |
| WO | WO-2005120097 A2 | 12/2005 | |
| WO | WO-2006021154 A1 | 3/2006 | |
| WO | WO-2006066583 A1 | 6/2006 | |
| WO | WO-2006066585 A2 | 6/2006 | |
| WO | WO-2006071711 A2 | 7/2006 | |
| WO | WO-2006099120 A2 | 9/2006 | |
| WO | WO-2006108304 A1 | 10/2006 | |

(56) References Cited

FOREIGN PATENT DOCUMENTS

| | | |
|---|---|---|
| WO | WO-2006108858 A1 | 10/2006 |
| WO | WO-2006111109 A1 | 10/2006 |
| WO | WO-2007027490 A2 | 3/2007 |
| WO | WO-2007035646 A2 | 3/2007 |
| WO | WO-2007127879 A2 | 11/2007 |
| WO | WO-2007133478 A2 | 11/2007 |
| WO | WO-2007137869 A2 | 12/2007 |
| WO | WO-2008010012 A2 | 1/2008 |
| WO | WO-2008036344 A1 | 3/2008 |
| WO | WO-2008062382 A2 | 5/2008 |
| WO | WO-2008116295 A1 | 10/2008 |
| WO | WO-2008150633 A2 | 12/2008 |
| WO | WO-2009140669 A2 | 11/2009 |
| WO | WO-2009145437 A2 | 12/2009 |
| WO | WO-2010017484 A2 | 2/2010 |
| WO | WO-2010025166 A1 | 3/2010 |
| WO | WO-2010025467 A1 | 3/2010 |
| WO | WO-2010078558 A1 | 7/2010 |
| WO | WO-2010085033 A2 | 7/2010 |
| WO | WO-2010132617 A2 | 11/2010 |
| WO | WO-2010145780 A1 | 12/2010 |
| WO | WO-2011005633 A2 | 1/2011 |
| WO | WO-2011026411 A1 | 3/2011 |
| WO | WO-2011039676 A2 | 4/2011 |
| WO | WO-2011046860 A2 | 4/2011 |
| WO | WO-2011047334 A1 | 4/2011 |
| WO | WO-2011123933 A1 | 10/2011 |
| WO | WO-2011137230 A1 | 11/2011 |
| WO | WO-2012057881 A1 | 5/2012 |
| WO | WO-2012116603 A1 | 9/2012 |
| WO | WO-2012127281 A1 | 9/2012 |
| WO | WO-2013026999 A1 | 2/2013 |
| WO | WO-2013036853 A2 | 3/2013 |
| WO | WO-2013061887 A1 | 5/2013 |
| WO | WO-2013102855 A1 | 7/2013 |
| WO | WO-2013109517 A1 | 7/2013 |
| WO | WO-2013138182 A1 | 9/2013 |
| WO | WO-2013141870 A1 | 9/2013 |
| WO | WO-2013155193 A1 | 10/2013 |
| WO | WO-2013175076 A1 | 11/2013 |
| WO | WO-2014015215 A2 | 1/2014 |
| WO | WO-2014018786 A2 | 1/2014 |
| WO | WO-2014075494 A1 | 5/2014 |
| WO | WO-2014089086 A1 | 6/2014 |
| WO | WO-2014100036 A1 | 6/2014 |
| WO | WO-2014106056 A2 | 7/2014 |
| WO | WO-2014123846 A1 | 8/2014 |
| WO | WO-2014133822 A2 | 9/2014 |
| WO | WO-2014141221 A2 | 9/2014 |
| WO | WO-2014145496 A1 | 9/2014 |
| WO | WO-2014150255 A2 | 9/2014 |
| WO | WO-2014152963 A1 | 9/2014 |
| WO | WO-2014189070 A1 | 11/2014 |
| WO | WO-2014009876 A3 | 12/2014 |
| WO | WO-2015019273 A2 | 2/2015 |
| WO | WO-2015023515 A1 | 2/2015 |
| WO | WO-2015025482 A1 | 2/2015 |
| WO | WO-2015026387 A1 | 2/2015 |
| WO | WO-2015050816 A1 | 4/2015 |
| WO | WO-2015078112 A1 | 6/2015 |
| WO | WO-2015085249 A1 | 6/2015 |
| WO | WO-2015091070 A1 | 6/2015 |
| WO | WO-2015124670 A1 | 8/2015 |
| WO | WO-2015132528 A1 | 9/2015 |
| WO | WO-2015140801 A2 | 9/2015 |
| WO | WO-2015143099 A2 | 9/2015 |
| WO | WO-2015145455 A1 | 10/2015 |
| WO | WO-2015156143 A1 | 10/2015 |
| WO | WO-2015164787 A1 | 10/2015 |
| WO | WO-2015179915 A1 | 12/2015 |
| WO | WO-2015179916 A1 | 12/2015 |
| WO | WO-2015179917 A1 | 12/2015 |
| WO | WO-2015181836 A2 | 12/2015 |
| WO | WO-2015187480 A1 | 12/2015 |
| WO | WO-2016001088 A1 | 1/2016 |
| WO | WO-2016006536 A1 | 1/2016 |
| WO | WO 2016/019191 | 2/2016 |
| WO | WO-2016018448 A1 | 2/2016 |
| WO | WO-2016019191 A1 * | 2/2016 | ......... G06F 19/3481 |
| WO | WO-2016075656 A1 | 5/2016 |
| WO | WO-2016108163 A1 | 7/2016 |
| WO | WO-2016109041 A1 | 7/2016 |
| WO | WO-2016118318 A1 | 7/2016 |
| WO | WO-2016120820 A2 | 8/2016 |
| WO | WO-2016136694 A1 | 9/2016 |
| WO | WO-2016141799 A1 | 9/2016 |
| WO | WO-2016151364 A1 | 9/2016 |
| WO | WO-2016160849 A1 | 10/2016 |
| WO | WO-2016175649 A1 | 11/2016 |
| WO | WO-2016178936 A1 | 11/2016 |
| WO | WO-2016190978 A1 | 12/2016 |
| WO | WO-2017001848 A1 | 1/2017 |
| WO | WO-2017004423 A1 | 1/2017 |
| WO | WO-2017027729 A2 | 2/2017 |
| WO | WO-2017035024 A1 | 3/2017 |
| WO | WO-2017053384 A1 | 3/2017 |
| WO | WO-2017062042 A1 | 4/2017 |
| WO | WO-2017142100 A1 | 8/2017 |
| WO | WO-2017165895 A1 | 9/2017 |
| WO | WO-2017192673 A1 | 11/2017 |
| WO | WO-2018007100 A1 | 1/2018 |
| WO | WO-2018013666 A1 | 1/2018 |
| WO | WO-2018033819 A1 | 2/2018 |
| WO | WO-2018044894 A1 | 3/2018 |
| WO | WO-2018064077 A2 * | 4/2018 | ......... A61F 13/0253 |
| WO | WO-2018064234 A1 | 4/2018 |
| WO | WO-2018067593 A2 | 4/2018 |
| WO | WO-2018082813 A1 | 5/2018 |
| WO | WO-2018091492 A1 | 5/2018 |
| WO | WO-2018096390 A1 | 5/2018 |
| WO | WO-2018145880 A1 | 8/2018 |
| WO | WO 2018/165049 | 9/2018 |

OTHER PUBLICATIONS

Cinterion., "Cinterion PHS8-P 3G HSPA+," retrieved from http://www.cinterion.com/tl_files/cinterion/downloads/cinterion_datasheet_PHSS_web.pdf, 2012, 2 pages.

Gannon M., "Selecting the Correct Spring-Loaded Connector for Modern Interconnect Applications," Retrieved from https://www.connectortips.com/selecting-correct-spring-loaded-connector-modern-interconnect-applications/, Jun. 30, 2017, 6 pages.

IEC, "Medical electrical equipment—Part 1: General requirements for basic safety and essential performance," IEC 60601-1, Jul. 2012, 236 pages.

IEC, "Medical electrical equipment—Part 1: General requirements for basic safety and essential performance," IEC 60601-1, Dec. 2005, 786 pages.

International Preliminary Report on Patentability for Application No. PCT/US2018/020969, dated Sep. 19, 2019, 7 pages.

Melone L., "Nylon Fasteners: What are They and How are They Used?," retrieved from https://www.melfast.com/blog/2015/07/nylon-fasteners-what-are-they-and-how-are-they-used, Jul. 27, 2015, 7 pages.

Straka F., "What is Driving the Growth of Power over Ethernet?," retrieved from http://panduitblog.com/2015/12/17/enterprise/driving-growth-power-ethernet/, Dec. 17, 2015, 6 pages.

Wikipedia, "Antenna (radio)," https://en.wikipedia.org/wiki/Antenna_(radio), accessed on May 3, 2021, 20 pages.

International Search Report and Written Opinion, re PCT Application No. PCT/US2018/020969, dated Jun. 25, 2018.

U.S. Appl. No. 16/334,563, Construction and Protection of Components in Negative Pressure Wound Therapy Systems, filed Mar. 19, 2019.

U.S. Appl. No. 17/848,978, Construction and Protection of Components in Negative Pressure Wound Therapy Systems, filed Jun. 24, 2022.

Communication of a Notice of Opposition for the European Patent No. 3592313, dated Apr. 19, 2022, 37 pages.

(56) References Cited

OTHER PUBLICATIONS

Communication of Further Notices of Opposition Pursuant to Rule 79(2) EPC for the European Patent No. 3592313, dated Apr. 29, 2022, 2 pages.
Merriam-Webster, "Definition of Board," retrieved from the Internet: URL: https://www.merriam-webster.com/dictionary/board, on May 17, 2022, 10 pages.
Styger E., "Tutorial: Web Server with the ESP8266 WiFi Module," DZone, Dec. 2, 2014, 71 pages, Retrieved from the Internet: URL: https://dzone.com/articles/tutorial-web-server-esp8266.
The Wayback Machine, "Tutorial : ESP12E, getting started with the ESP8266 module," Retrieved on May 19, 2022, 54 pages, Retrieved from the Internet: URL: https://www.mikrocontroller-elektronik.de/esp12e-tutorial-einstieg-mit-dem-esp8266-modul/.
Wikipedia, "Ground (electricity)," retrieved from the Internet: URL: https://en.wikipedia.org/wiki/Ground_(electricity), on May 17, 2022, 7 pages.
Brief Communication—Letter from the Opponent of Jan. 19, 2023, for European Patent No. 3592313, dated Jan. 25, 2023, 6 pages.
Brief Communication—Letter from the Proprietor of Mar. 22, 2023, for the European Patent No. 3592313, dated Mar. 29, 2023, 5 pages.
Merriam-Webster, "Trace," Retrieved from https://www.merriam-webster.com/dictionary/trace, on Mar. 3, 2023, 14 pages.
Reply of the Patent Proprietor to the Notice of Opposition, re the Opposition of European Patent No. 3592313, dated Aug. 26, 2022, 13 pages.
Transmittal of Decision Summons for the Opposition of European Patent No. 3592313, mailed on Jun. 2, 2023, 11 pages.
Brief Communication—Letter from the Opponent of Jan. 10, 2024, for European Patent No. 3592313, dated Jan. 15, 2024, 6 pages.
Written Submission in Preparation for the Oral Proceedings, for the Opposition of European Patent No. 3592313, dated Feb. 9, 2024, 18 pages.

\* cited by examiner

REDUCED PRESSURE THERAPY SYSTEMS AND METHODS INCLUDING AN ANTENNA

CROSS-REFERENCE TO RELATED APPLICATIONS

This application is a U.S. national stage application of International Patent Application No. PCT/US2018/020969, filed Mar. 5, 2018, which claims the benefit of U.S. Provisional Application No. 62/468,358, filed Mar. 7, 2017; the disclosure of which is hereby incorporated by reference in its entirety.

BACKGROUND

Embodiments of the present disclosure relate to methods and apparatuses for dressing and treating a wound with negative or reduced pressure therapy or topical negative pressure (TNP) therapy. In particular, but without limitation, embodiments disclosed herein relate to negative pressure therapy devices, methods for controlling the operation of TNP systems, and methods of using TNP systems.

SUMMARY

In some embodiments, an apparatus for applying negative pressure to a wound is disclosed. The apparatus can include: a housing; a negative pressure source positioned within the housing and configured to provide negative pressure via a fluid flow path to a wound dressing; a communications board positioned within the housing, the communications board including a controller configured to transmit and receive data from a remote electronic device; and an antenna board positioned within the housing and mechanically mounted to the communications board and electrically connected to the communications board. The antenna board can include an antenna electrically coupled to the controller, and the antenna can wirelessly transmit and receive signals for the controller. The antenna can include a conductive area located on the antenna board and a ground area located on the communications board.

The apparatus of the preceding paragraph can include one or more of the following features: The conductive area can include a conductive trace, and the ground area can include a ground plane. The ground plane of the antenna is connected to a ground plane of the communications board. The ground plane of the antenna can be electrically connected to the ground plane of the communications board via a shunt. The ground plane can be divided into a first portion and a second portion, and the first portion be can electrically connected to the shunt, a length of the first portion controlling a first bandwidth of the antenna. A length of the second portion can control a second bandwidth of the antenna, the second bandwidth being different from the first bandwidth. The conductive trace can include first and second conductive trace portions configured to receive and transmit signals in high and narrow bands. The first conductive trace portion associated with the high band can have a greater surface area than the second conductive trance portion associated with the narrow band. The antenna board can be electrically connected to the communications board via a single antenna connector on the communications board. The antenna connector on the communications board can include a protrusion electrically connected to the antenna board via a hole in the antenna board. The antenna connector can provide a connection for signal feed and ground. The antenna board can be a printed circuit board. The antenna can be a planar inverted F-antenna. The antenna can be a dual-band cellular antenna. The antenna board can be positioned so that the conductive area faces away from the communications board. The apparatus can further include a canister configured to store at least some fluid removed from the wound, and the antenna board can be positioned so that the conductive area faces the canister.

A method of operating, using, or manufacturing the apparatus of the preceding two paragraphs is also disclosed.

BRIEF DESCRIPTION OF THE DRAWINGS

Features and advantages of the present disclosure will be apparent from the following detailed description, taken in conjunction with the accompanying drawings of which.

DETAILED DESCRIPTION

The present disclosure relates to methods and apparatuses for dressing and treating a wound with reduced pressure therapy or topical negative pressure (TNP) therapy. In particular, but without limitation, embodiments of this disclosure relate to negative pressure therapy apparatuses, methods for controlling the operation of TNP systems, and methods of using TNP systems. The methods and apparatuses can incorporate or implement any combination of the features described below.

Many different types of wound dressings are known for aiding in the healing process of a human or animal. These different types of wound dressings include many different types of materials and layers, for example, gauze, pads, foam pads or multi-layer wound dressings. TNP therapy, sometimes referred to as vacuum assisted closure, negative pressure wound therapy, or reduced pressure wound therapy, can be a beneficial mechanism for improving the healing rate of a wound. Such therapy is applicable to a broad range of wounds such as incisional wounds, open wounds and abdominal wounds or the like.

TNP therapy can assist in the closure and healing of wounds by reducing tissue oedema, encouraging blood flow, stimulating the formation of granulation tissue, removing excess exudates, and reducing bacterial load and thus, infection to the wound. Furthermore, TNP therapy can permit less outside disturbance of the wound and promote more rapid healing.

As is used herein, reduced or negative pressure levels, such as −X mmHg, represent pressure levels that are below atmospheric pressure, which typically corresponds to 760 mmHg (or 1 atm, 29.93 inHg, 101.325 kPa, 14.696 psi, etc.). Accordingly, a negative pressure value of −X mmHg reflects pressure that is X mmHg below atmospheric pressure, such as a pressure of (760−X) mmHg. In addition, negative pressure that is "less" or "smaller" than −X mmHg corresponds to pressure that is closer to atmospheric pressure (for example, −40 mmHg is less than −60 mmHg). Negative pressure that is "more" or "greater" than −X mmHg corresponds to pressure that is further from atmospheric pressure (for example, −80 mmHg is more than −60 mmHg).

System Overview

A pump assembly can include one or more features that improve the tolerance of the pump assembly to environmental conditions, such as high temperature, high altitude, electromagnetic radiation, or electrostatic discharge (ESD). The improved tolerance of the pump assembly can, for example, enable the pump assembly to function despite non-ideal environmental conditions or function more safely in the presence of certain environmental conditions. The pump assembly can be small, compact, and light and capable of transmitting and receiving wireless communications and able to meet stringent electrical immunity standards. Although one or more features are described separately, in some instances, one or more of the features can be combined in particular implementations of pump assemblies.

Figure 1:
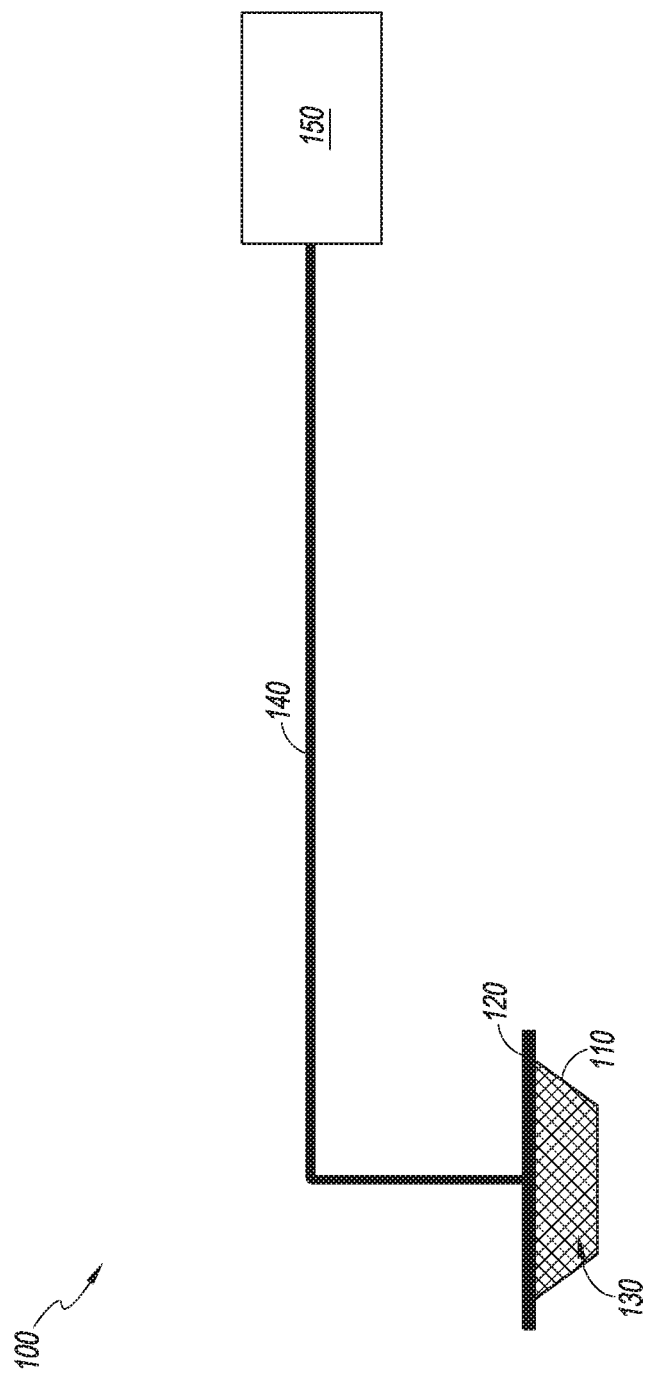
FIG. 1 illustrates a reduced pressure wound therapy system according to some embodiments.

FIG. 1 illustrates an embodiment of a negative or reduced pressure wound treatment (or TNP) system 100 comprising a wound filler 130 placed inside a wound cavity 110, the wound cavity sealed by a wound cover 120. The wound filler 130 in combination with the wound cover 120 can be referred to as wound dressing. A single or multi lumen tube or conduit 140 is connected the wound cover 120 with a pump assembly 150 configured to supply reduced pressure. The wound cover 120 can be in fluidic communication with the wound cavity 110. In any of the system embodiments disclosed herein, as in the embodiment illustrated in FIG. 1, the pump assembly can be a canisterless pump assembly (meaning that exudate is collected in the wound dressing or is transferred via tube 140 for collection to another location). However, any of the pump assembly embodiments disclosed herein can be configured to include or support a canister. Additionally, in any of the system embodiments disclosed herein, any of the pump assembly embodiments can be mounted to or supported by the dressing, or adjacent to the dressing.

The wound filler 130 can be any suitable type, such as hydrophilic or hydrophobic foam, gauze, inflatable bag, and so on. The wound filler 130 can be conformable to the wound cavity 110 such that it substantially fills the cavity. The wound cover 120 can provide a substantially fluid impermeable seal over the wound cavity 110. The wound cover 120 can have a top side and a bottom side, and the bottom side adhesively (or in any other suitable manner) seals with wound cavity 110. The conduit 140 or lumen or any other conduit or lumen disclosed herein can be formed from polyurethane, PVC, nylon, polyethylene, silicone, or any other suitable material.

Some embodiments of the wound cover 120 can have a port (not shown) configured to receive an end of the conduit 140. For example, the port can be Renays Soft Port available from Smith & Nephew. In other embodiments, the conduit 140 can otherwise pass through and/or under the wound cover 120 to supply reduced pressure to the wound cavity 110 so as to maintain a desired level of reduced pressure in the wound cavity. The conduit 140 can be any suitable article configured to provide at least a substantially sealed fluid flow pathway between the pump assembly 150 and the wound cover 120, so as to supply the reduced pressure provided by the pump assembly 150 to wound cavity 110.

The wound cover 120 and the wound filler 130 can be provided as a single article or an integrated single unit. In some embodiments, no wound filler is provided and the wound cover by itself may be considered the wound dressing. The wound dressing may then be connected, via the conduit 140, to a source of negative pressure, such as the pump assembly 150. The pump assembly 150 can be miniaturized and portable, although larger conventional pumps such can also be used.

The wound cover 120 can be located over a wound site to be treated. The wound cover 120 can form a substantially sealed cavity or enclosure over the wound site. In some embodiments, the wound cover 120 can be configured to have a film having a high water vapour permeability to enable the evaporation of surplus fluid, and can have a superabsorbing material contained therein to safely absorb wound exudate. It will be appreciated that throughout this specification reference is made to a wound. In this sense it is to be understood that the term wound is to be broadly construed and encompasses open and closed wounds in which skin is torn, cut or punctured or where trauma causes a contusion, or any other surficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. The components of the TNP system described herein can be particularly suited for incisional wounds that exude a small amount of wound exudate.

Some embodiments of the system are designed to operate without the use of an exudate canister. Some embodiments can be configured to support an exudate canister. In some embodiments, configuring the pump assembly 150 and tubing 140 so that the tubing 140 can be quickly and easily removed from the pump assembly 150 can facilitate or improve the process of dressing or pump changes, if necessary. Any of the pump embodiments disclosed herein can be configured to have any suitable connection between the tubing and the pump.

The pump assembly 150 can be configured to deliver negative pressure of approximately −80 mmHg, or between about −20 mmHg and 200 mmHg in some implementations. Note that these pressures are relative to normal ambient atmospheric pressure thus, −200 mmHg would be about 560 mmHg in practical terms. The pressure range can be between about −40 mmHg and −150 mmHg. Alternatively a pressure range of up to −75 mmHg, up to −80 mmHg or over −80 mmHg can be used. Also a pressure range of below −75 mmHg can be used. Alternatively a pressure range of over approximately −100 mmHg, or even 150 mmHg, can be supplied by the pump assembly 150.

In operation, the wound filler 130 is inserted into the wound cavity 110 and wound cover 120 is placed so as to seal the wound cavity 110. The pump assembly 150 provides a source of a negative pressure to the wound cover 120, which is transmitted to the wound cavity 110 via the wound filler 130. Fluid (e.g., wound exudate) is drawn through the conduit 140, and can be stored in a canister. In some embodiments, fluid is absorbed by the wound filler 130 or one or more absorbent layers (not shown).

Wound dressings that may be utilized with the pump assembly and other embodiments of the present application include Renasys-F, Renasys-G, Renasys Aft and Pico Dressings available from Smith & Nephew. Further description of such wound dressings and other components of a negative pressure wound therapy system that may be used with the pump assembly and other embodiments of the present application are found in U.S. Patent Publication Nos. 2011/0213287, 2011/0282309, 2012/0116334, 2012/0136325, and 2013/0110058, which are incorporated by reference in their entirety. In other embodiments, other suitable wound dressings can be utilized.

Figure 2A:
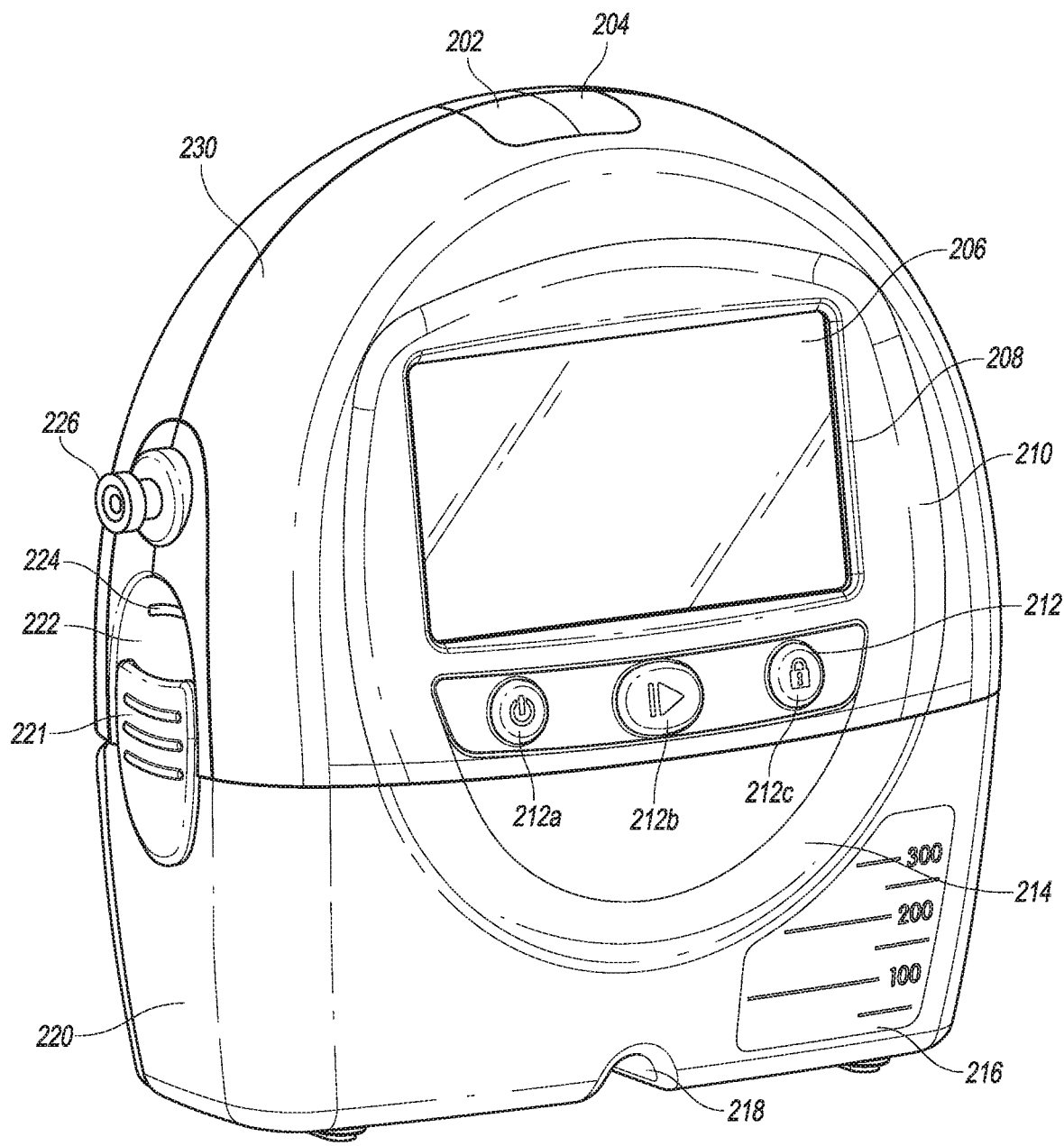
FIGS. 2A, 2B, and 2C illustrate a pump assembly and canister according to some embodiments.

FIG. 2A illustrates a front view of a pump assembly 230 and canister 220 according to some embodiments. As is illustrated, the pump assembly 230 and the canister are connected, thereby forming a negative pressure wound therapy device. The pump assembly 230 can be similar to or the same as the pump assembly 150 in some embodiments.

The pump assembly 230 includes one or more indicators, such as visual indicator 202 configured to indicate alarms and visual indicator 204 configured to indicate status of the TNP system. The indicators 202 and 204 can be configured to alert a user, such as patient or medical care provider, to a variety of operating and/or failure conditions of the system, including alerting the user to normal or proper operating conditions, pump failure, power supplied to the pump or power failure, detection of a leak within the wound cover or flow pathway, suction blockage, or any other similar or suitable conditions or combinations thereof. The pump assembly 230 can comprise additional indicators. The pump assembly can use a single indicator or multiple indicators. Any suitable indicator can be used such as visual, audio, tactile indicator, and so on. The indicator 202 can be configured to signal alarm conditions, such as canister full, power low, conduit 140 disconnected, seal broken in the wound seal 120, and so on. The indicator 202 can be configured to display red flashing light to draw user's attention. The indicator 204 can be configured to signal status of the TNP system, such as therapy delivery is ok, leak detected, and so on. The indicator 204 can be configured to display one or more different colors of light, such as green, yellow, etc. For example, green light can be emitted when the TNP system is operating properly and yellow light can be emitted to indicate a warning.

The pump assembly 230 includes a display or screen 206 mounted in a recess 208 formed in a case of the pump assembly. The display 206 can be a touch screen display. The display 206 can support playback of audiovisual (AV) content, such as instructional videos. As explained below, the display 206 can be configured to render a number of screens or graphical user interfaces (GUIs) for configuring, controlling, and monitoring the operation of the TNP system. The pump assembly 230 comprises a gripping portion 210 formed in the case of the pump assembly. The gripping portion 210 can be configured to assist the user to hold the pump assembly 230, such as during removal of the canister 220. The canister 220 can be replaced with another canister, such as when the canister 220 has been filled with fluid.

The pump assembly 230 includes one or more keys or buttons 212 configured to allow the user to operate and monitor the operation of the TNP system. As is illustrated, there buttons 212a, 212b, and 212c are included. Button 212a can be configured as a power button to turn on/off the pump assembly 230. Button 212b can be configured as a play/pause button for the delivery of negative pressure therapy. For example, pressing the button 212b can cause therapy to start, and pressing the button 212b afterward can cause therapy to pause or end. Button 212c can be configured to lock the display 206 and/or the buttons 212. For instance, button 212c can be pressed so that the user does not unintentionally alter the delivery of the therapy. Button 212c can be depressed to unlock the controls. In other embodiments, additional buttons can be used or one or more of the illustrated buttons 212a, 212b, or 212c can be omitted. Multiple key presses and/or sequences of key presses can be used to operate the pump assembly 230.

The pump assembly 230 includes one or more latch recesses 222 formed in the cover. In the illustrated embodiment, two latch recesses 222 can be formed on the sides of the pump assembly 230. The latch recesses 222 can be configured to allow attachment and detachment of the canister 220 using one or more canister latches 221. The pump assembly 230 comprises an air outlet 224 for allowing air removed from the wound cavity 110 to escape. Air entering the pump assembly can be passed through one or more suitable filters, such as antibacterial filters. This can maintain reusability of the pump assembly. The pump assembly 230 includes one or more strap mounts 226 for connecting a carry strap to the pump assembly 230 or for attaching a cradle. In the illustrated embodiment, two strap mounts 226 can be formed on the sides of the pump assembly 230. In some embodiments, various of these features are omitted and/or various additional features are added to the pump assembly 230.

The canister 220 is configured to hold fluid (e.g., exudate) removed from the wound cavity 110. The canister 220 includes one or more latches 221 for attaching the canister to the pump assembly 230. In the illustrated embodiment, the canister 220 comprises two latches 221 on the sides of the canister. The exterior of the canister 220 can formed from frosted plastic so that the canister is substantially opaque and the contents of the canister and substantially hidden from plain view. The canister 220 comprises a gripping portion 214 formed in a case of the canister. The gripping portion 214 can be configured to allow the user to hold the pump assembly 220, such as during removal of the canister from the apparatus 230. The canister 220 includes a substantially transparent window 216, which can also include graduations of volume. For example, the illustrated 300 mL canister 220 includes graduations of 50 mL, 100 mL, 150 mL, 200 mL, 250 mL, and 300 mL. Other embodiments of the canister can hold different volume of fluid and can include different graduation scale. For example, the canister can be an 800 mL canister. The canister 220 comprises a tubing channel 218 for connecting to the conduit 140. In some embodiments, various of these features, such as the gripping portion 214, are omitted and/or various additional features are added to the canister 220. Any of the disclosed canisters may include or may omit a solidifier.

Figure 2B:
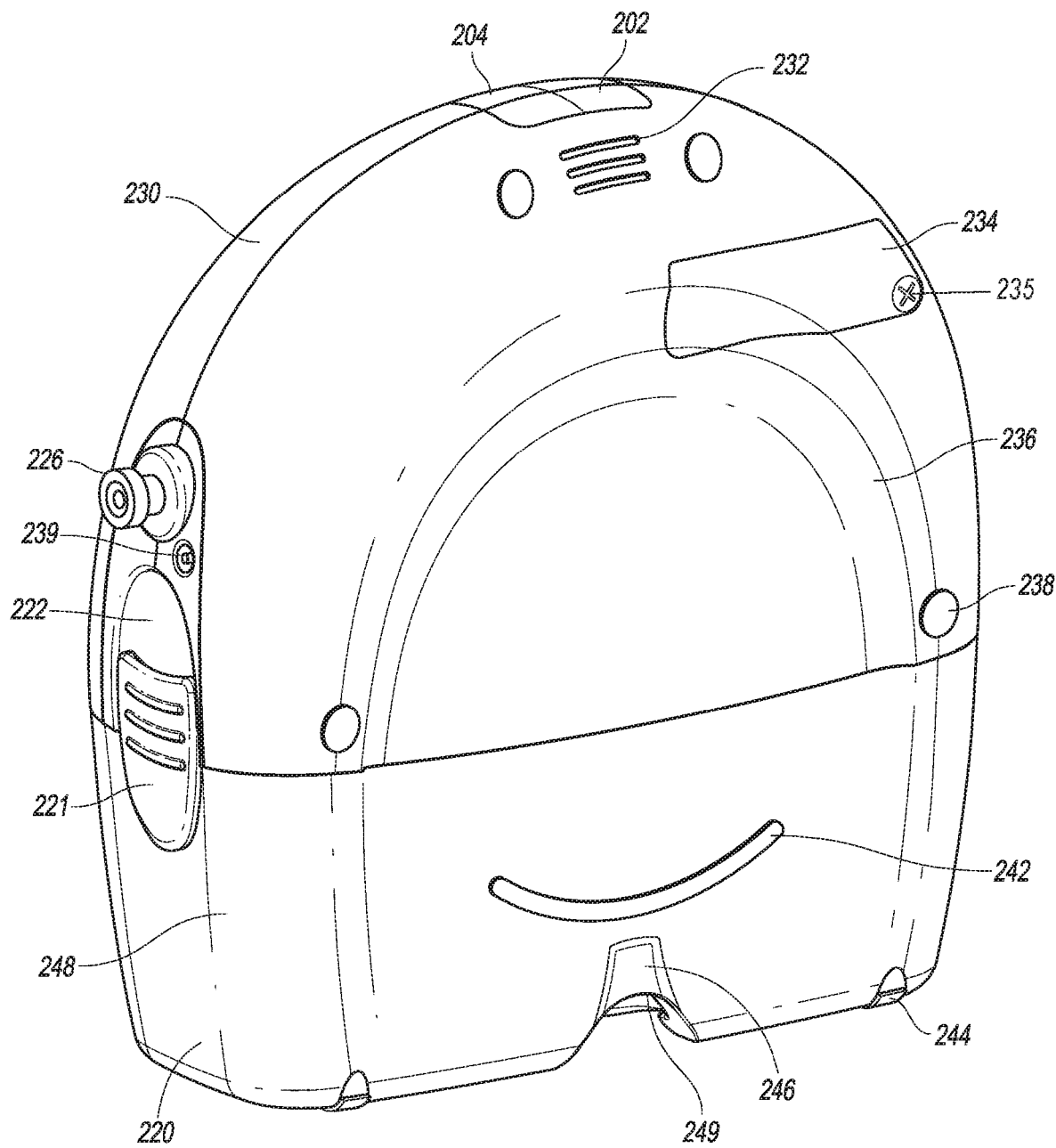

FIG. 2B illustrates a rear view of the pump assembly 230 and canister 220 according to some embodiments. The pump assembly 230 comprises a speaker port 232 for producing sound. The pump assembly 230 includes a filter access door 234 with a screw 235 for removing the access door 234, accessing, and replacing one or more filters, such as antibacterial or odor filters. The pump assembly 230 comprises a gripping portion 236 formed in the case of the pump assembly. The gripping portion 236 can be configured to allow the user to hold the pump assembly 230, such as during removal of the canister 220. The pump assembly 230 includes one or more covers 238 configured to as screw covers and/or feet or protectors for placing the pump assembly 230 on a surface. The covers 230 can be formed out of rubber, silicone, or any other suitable material. The pump assembly 230 comprises a power jack 239 for charging and recharging an internal battery of the pump assembly. The power jack 239 can be a direct current (DC) jack. In some embodiments, the pump assembly can comprise a disposable power source, such as batteries, so that no power jack is needed.

The canister 220 includes one or more feet 244 for placing the canister on a surface. The feet 244 can be formed out of rubber, silicone, or any other suitable material and can be angled at a suitable angle so that the canister 220 remains stable when placed on the surface. The canister 220 comprises a tube mount relief 246 configured to allow one or more tubes to exit to the front of the device. The canister 220 includes a stand or kickstand 248 for supporting the canister when it is placed on a surface. As explained below, the kickstand 248 can pivot between an opened and closed position. In closed position, the kickstand 248 can be latched to the canister 220. In some embodiments, the kickstand 248 can be made out of opaque material, such as plastic. In other embodiments, the kickstand 248 can be made out of transparent material. The kickstand 248 includes a gripping portion 242 formed in the kickstand. The gripping portion 242 can be configured to allow the user to place the kickstand 248 in the closed position. The kickstand 248 comprises a hole 249 to allow the user to place the kickstand in the open position. The hole 249 can be sized to allow the user to extend the kickstand using a finger.

Figure 2C:
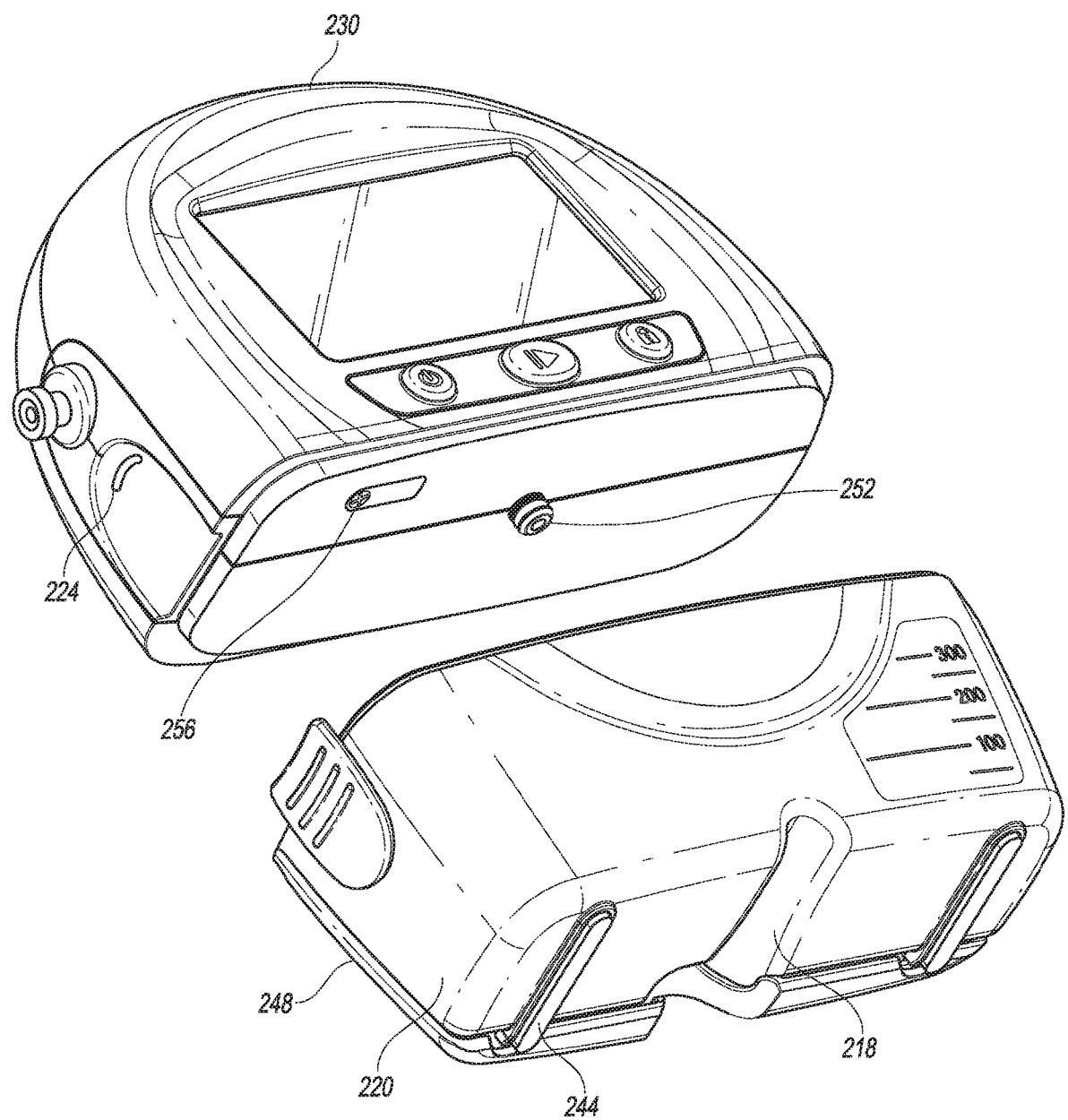

FIG. 2C illustrates a view of the pump assembly 230 separated from the canister 220 according to some embodiments. The pump assembly 230 includes a vacuum attachment, connector, or inlet 252 through which a vacuum pump communicates negative pressure to the canister 220. The pump assembly aspirates fluid, such as gas, from the wound via the inlet 252. The pump assembly 230 comprises a USB access door 256 configured to allow access to one or more USB ports. In some embodiments, the USB access door is omitted and USB ports are accessed through the door 234. The pump assembly 230 can include additional access doors configured to allow access to additional serial, parallel, and/or hybrid data transfer interfaces, such as SD, Compact Disc (CD), DVD, FireWire, Thunderbolt, PCI Express, and the like. In other embodiments, one or more of these additional ports are accessed through the door 234.

Figure 3:
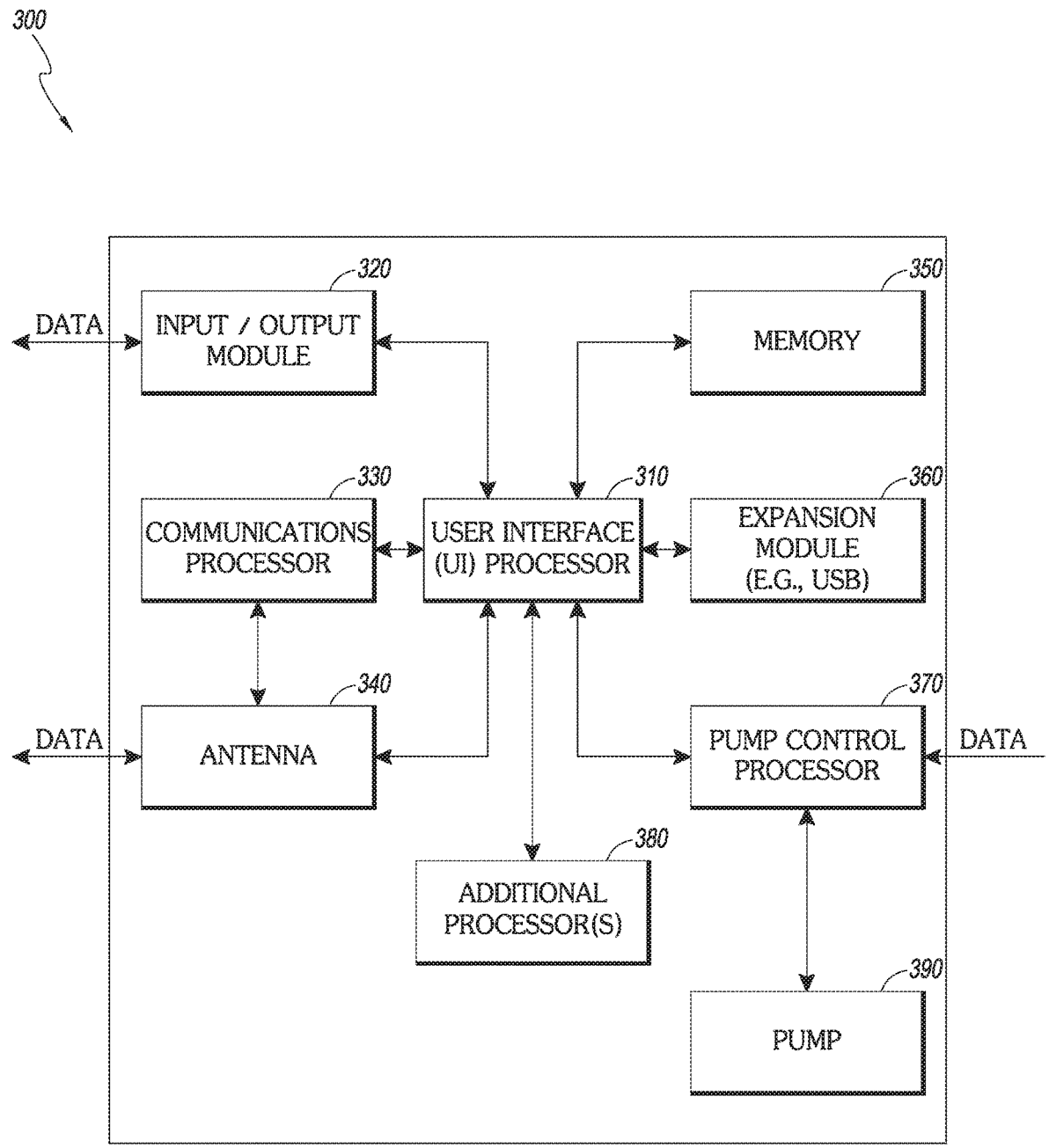
FIG. 3 illustrates an electrical component schematic of a pump assembly according to some embodiments.

FIG. 3 illustrates an electrical component schematic 300 of a pump assembly, such as the pump assembly 230, according to some embodiments. Electrical components can operate to accept user input, provide output to the user, operate the pump assembly and the TNP system, provide network connectivity, and so on. Electrical components can be mounted on one or more printed circuit boards (PCBs). As is illustrated, the pump assembly can include multiple processors.

The pump assembly can comprise a user interface processor or controller 310 configured to operate one or more components for accepting user input and providing output to the user, such as the display 206, buttons 212, etc. Input to the pump assembly and output from the pump assembly can controlled by an input/output (I/O) module 320. For example, the I/O module can receive data from one or more ports, such as serial, parallel, hybrid ports, and the like. The processor 310 also receives data from and provides data to one or more expansion modules 360, such as one or more USB ports, SD ports, Compact Disc (CD) drives, DVD drives, FireWire ports, Thunderbolt ports, PCI Express ports, and the like. The processor 310, along with other controllers or processors, stores data in one or more memory modules 350, which can be internal and/or external to the processor 310. Any suitable type of memory can be used, including volatile and/or non-volatile memory, such as RAM, ROM, magnetic memory, solid-state memory, magnetoresistive random-access memory (MRAM), and the like.

In some embodiments, the processor 310 can be a general purpose controller, such as a low-power processor. In other embodiments, the processor 310 can be an application specific processor. The processor 310 can be configured as a "central" processor in the electronic architecture of the pump assembly, and the processor 310 can coordinate the activity of other processors, such as a pump control processor 370, communications processor 330, and one or more additional processors 380 (e.g., processor for controlling the display 206, processor for controlling the buttons 212, etc.). The processor 310 can run a suitable operating system, such as a Linux, Windows CE, VxWorks, etc.

The pump control processor 370 can be configured to control the operation of a negative pressure pump 390. The pump 390 can be a suitable pump, such as a diaphragm pump, peristaltic pump, rotary pump, rotary vane pump, scroll pump, screw pump, liquid ring pump, diaphragm pump operated by a piezoelectric transducer, voice coil pump, and the like. The pump control processor 370 can measure pressure in a fluid flow path, using data received from one or more pressure sensors, calculate the rate of fluid flow, and control the pump. The pump control processor 370 can control a pump motor so that a desired level of negative pressure is achieved in the wound cavity 110. The desired level of negative pressure can be pressure set or selected by the user. In various embodiments, the pump control processor 370 controls the pump (e.g., pump motor) using pulse-width modulation (PWM). A control signal for driving the pump can be a 0-100% duty cycle PWM signal. The pump control processor 370 can perform flow rate calculations and detect various conditions in a flow path. The pump control processor 370 can communicate information to the processor 310. The pump control processor 370 can include internal memory and/or can utilize memory 350. The pump control processor 370 can be a low-power processor.

A communications processor 330 can be configured to provide wired and/or wireless connectivity. The communications processor 330 can utilize one or more antennas 340 for sending and receiving data. The communications processor 330 can provide one or more of the following types of connections: Global Positioning System (GPS) technology, cellular connectivity (e.g., 2G, 3G, LTE, 4G), WiFi connectivity, Internet connectivity, and the like. Connectivity can be used for various activities, such as pump assembly location tracking, asset tracking, compliance monitoring, remote selection, uploading of logs, alarms, and other operational data, and adjustment of therapy settings, upgrading of software and/or firmware, and the like. The communications processor 330 can provide dual GPS/cellular functionality. Cellular functionality can, for example, be 3G functionality. The pump assembly can include a SIM card, and SIM-based positional information can be obtained.

The communications processor 330 can communicate information to the processor 310. The communications processor 330 can include internal memory and/or can utilize memory 350. The communications processor 330 can be a low-power processor.

In some embodiments, using the connectivity provided by the communications processor 330, the device can upload any of the data stored, maintained, and/or tracked by the pump assembly. The device can also download various operational data, such as therapy selection and parameters, firmware and software patches and upgrades, and the like.

Figure 4A:
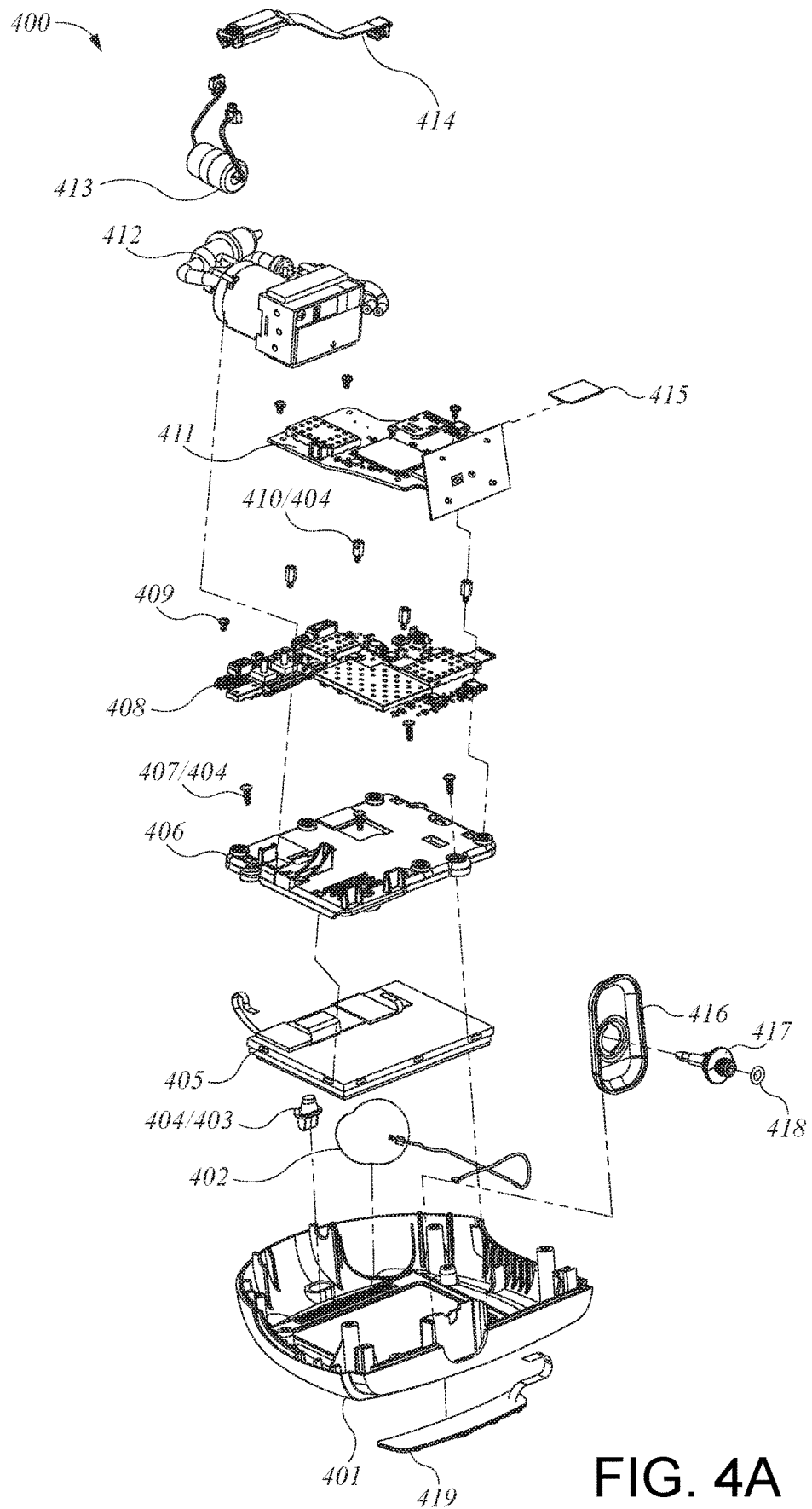
FIGS. 4A, 4B, 4C, 4D, 4E, and 4F illustrate a pump assembly according to some embodiments.
Figure 4B:
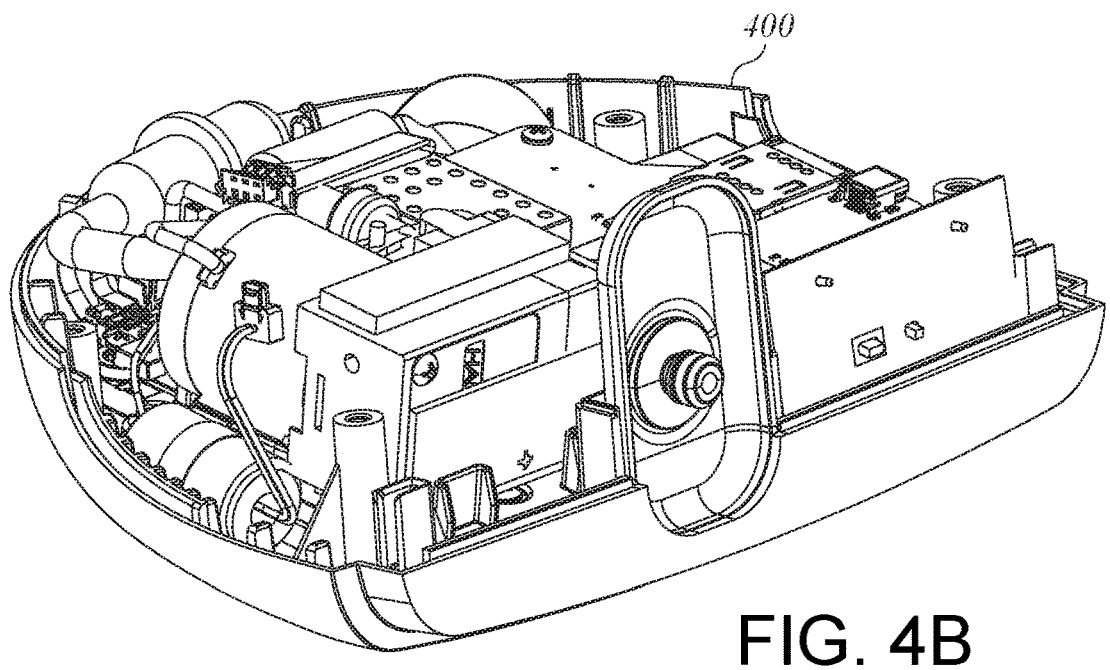
Figure 4C:
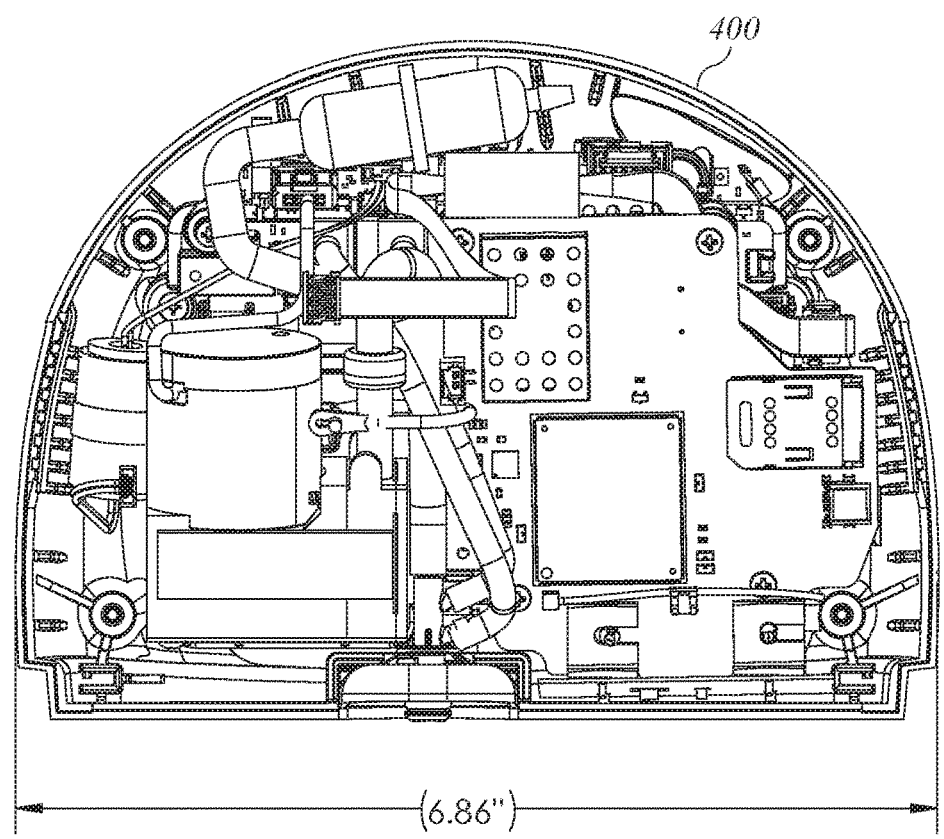
Figure 4D:
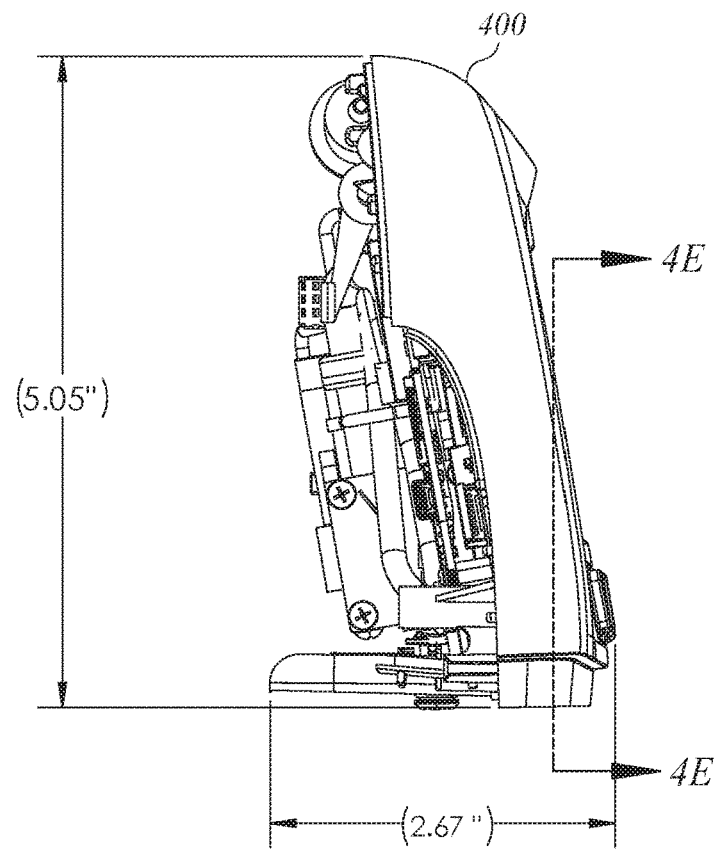
Figure 4E:
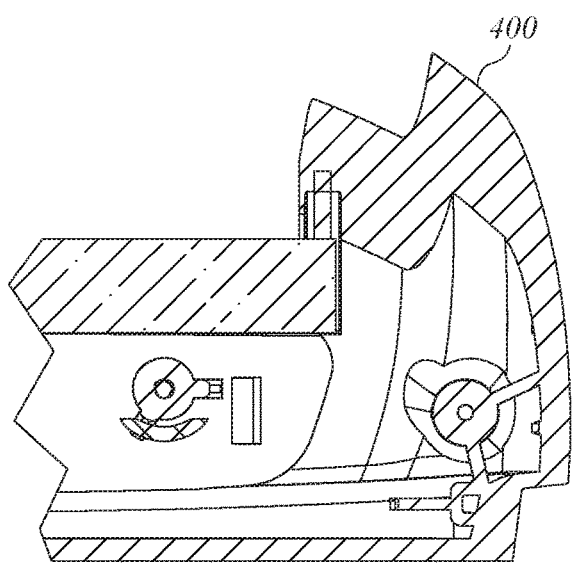
Figure 4F:
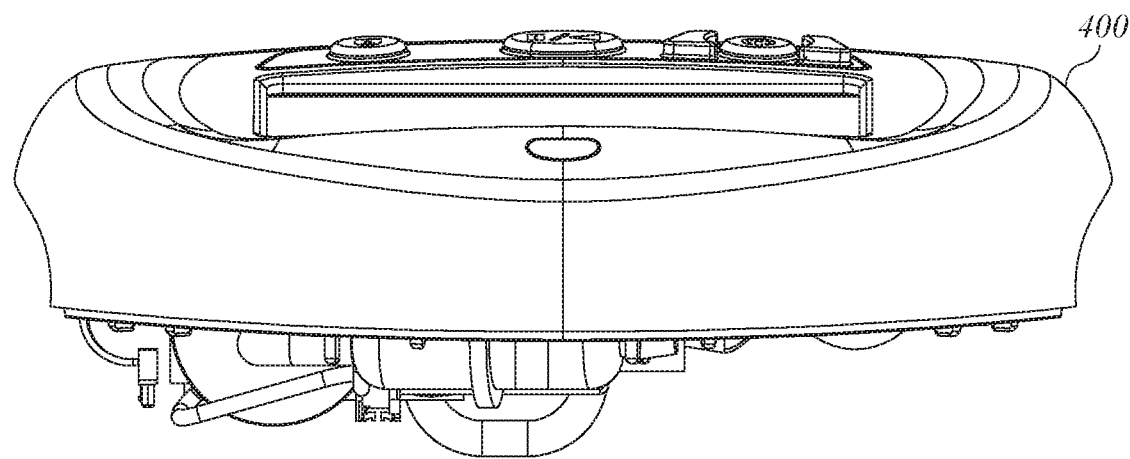

FIG. 4A illustrates exploded view of a pump assembly 400, such as the pump assembly 230, according to some embodiments. The illustrated view can correspond to the front portion of the pump assembly 400. The components of the pump assembly 400 can include: a front enclosure 401, a GPS antenna 402, a status light pipe 403, adhesives 404, a liquid crystal display (LCD) 405, a chassis and LCD circuit board assembly 406, screws 407, a main circuit board assembly 408, screws 409, standoffs 410, a communications circuit board assembly 411 (including a communications antenna), a negative pressure source 412, a power entry cable 413, a universal serial bus (USB) cable assembly 414, a subscriber identity module (SIM) card 415, a bottom enclosure 416, a canister connector 417, a canister connector O-ring 418, and a keypad 419. FIGS. 4B-4F illustrate multiple views of the pump assembly 400 according to some embodiments. The dimensions included in FIGS. 4B-4F are provided in inches.

Although FIGS. 4A-4F show particular components included as part of the pump assembly 400, some components may be removed or other components may be added in other implementations.

Figure 5A:
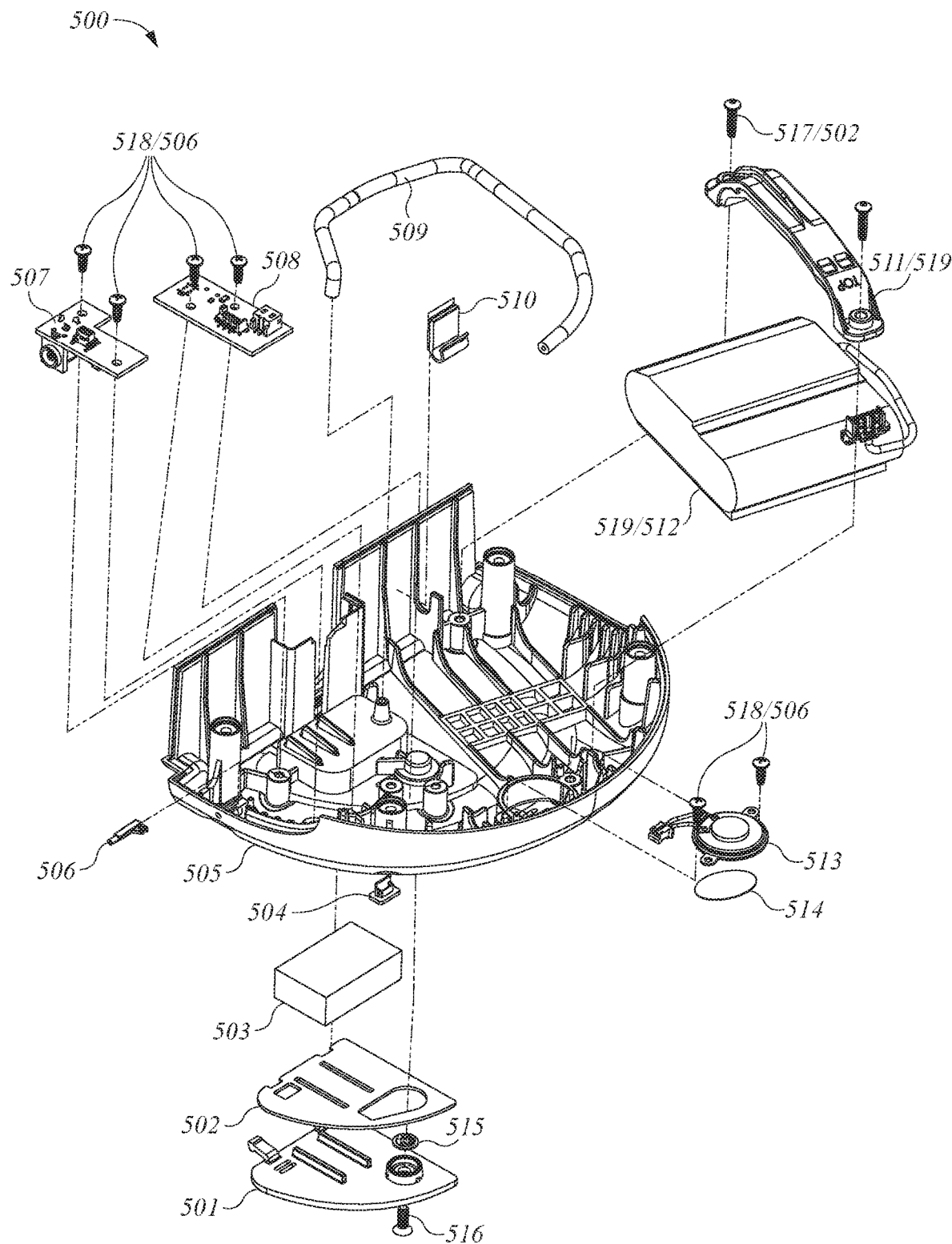
FIGS. 5A, 5B, 5C, 5D, and 5E illustrate a pump assembly according to some embodiments.
Figure 5B:
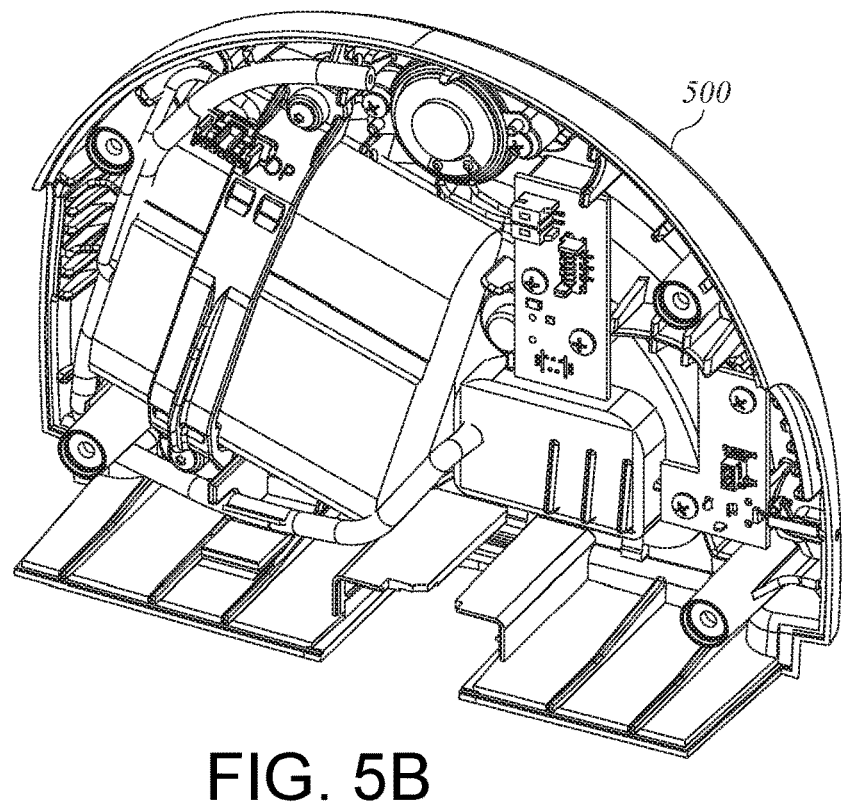
Figure 5C:
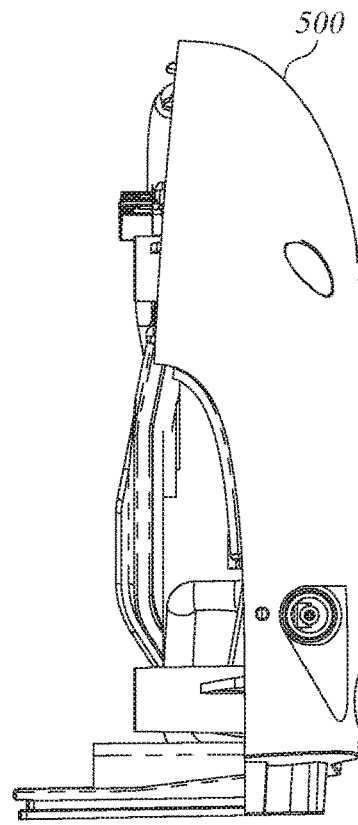
Figure 5D:
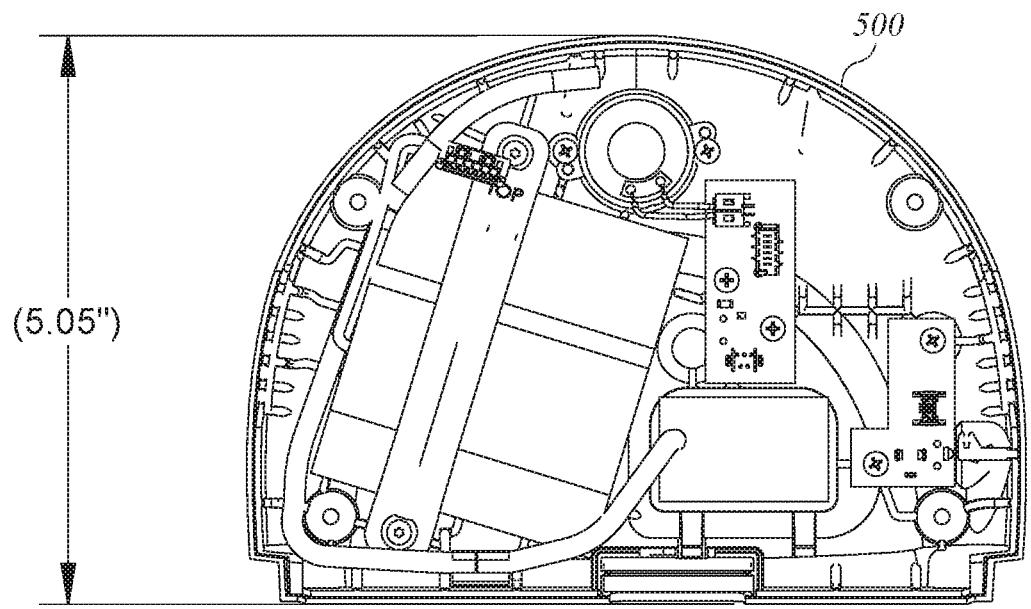
Figure 5E:
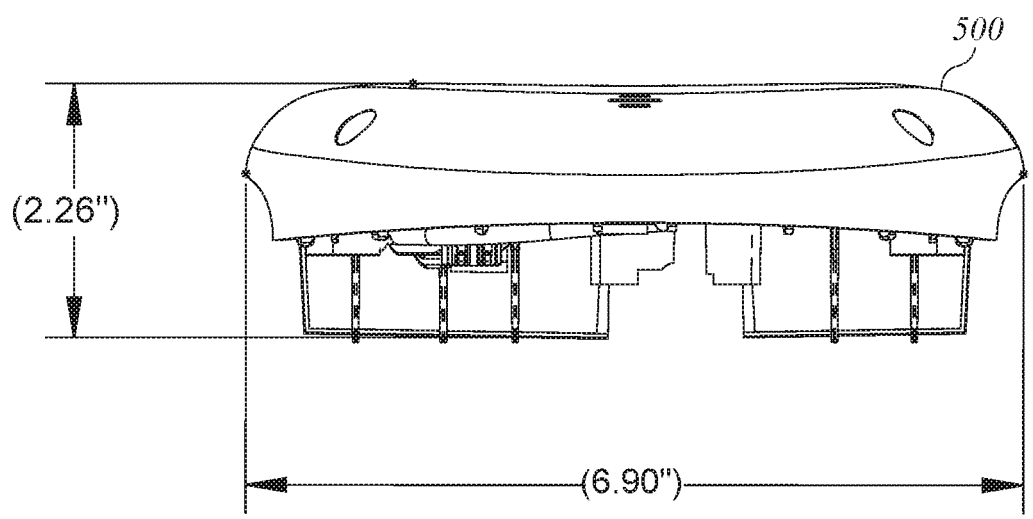

FIG. 5A illustrates exploded view of a pump assembly 500, such as the pump assembly 230, according to some embodiments. The illustrated view can correspond to the back portion of the pump assembly 500. The illustrated components of the pump assembly 500 can be configured to couple to the components of the pump assembly 400 to form an integral pump assembly. The components of the pump assembly 500 can include: an access door 501 (which can be the same as access door 234), a filter enclosure gasket 502, a filter 503 (for example, antibacterial filter, odor filter, and the like), a mini USB port cover 504, a back enclosure 505, a power entry light pipe 506, a power entry circuit board assembly 507, a USB circuit board assembly 508, a tubing outlet 509, a clip 510, a battery bracket 511, a battery 512, a speaker assembly 513, a speaker filter 514, a push nut 515, a screw 516 (which can be the same as the screw 235), screws 517, screws 518, and foam tape 519. FIGS. 5B-5E illustrate multiple views of the pump assembly 500 according to some embodiments. The dimensions included in FIGS. 5B-5E are provided in inches.

Although FIGS. 5A-5F show particular components included as part of the pump assembly 500, some components may be removed or other components may be added in other implementations.

Communications Electronics

Figure 6A:
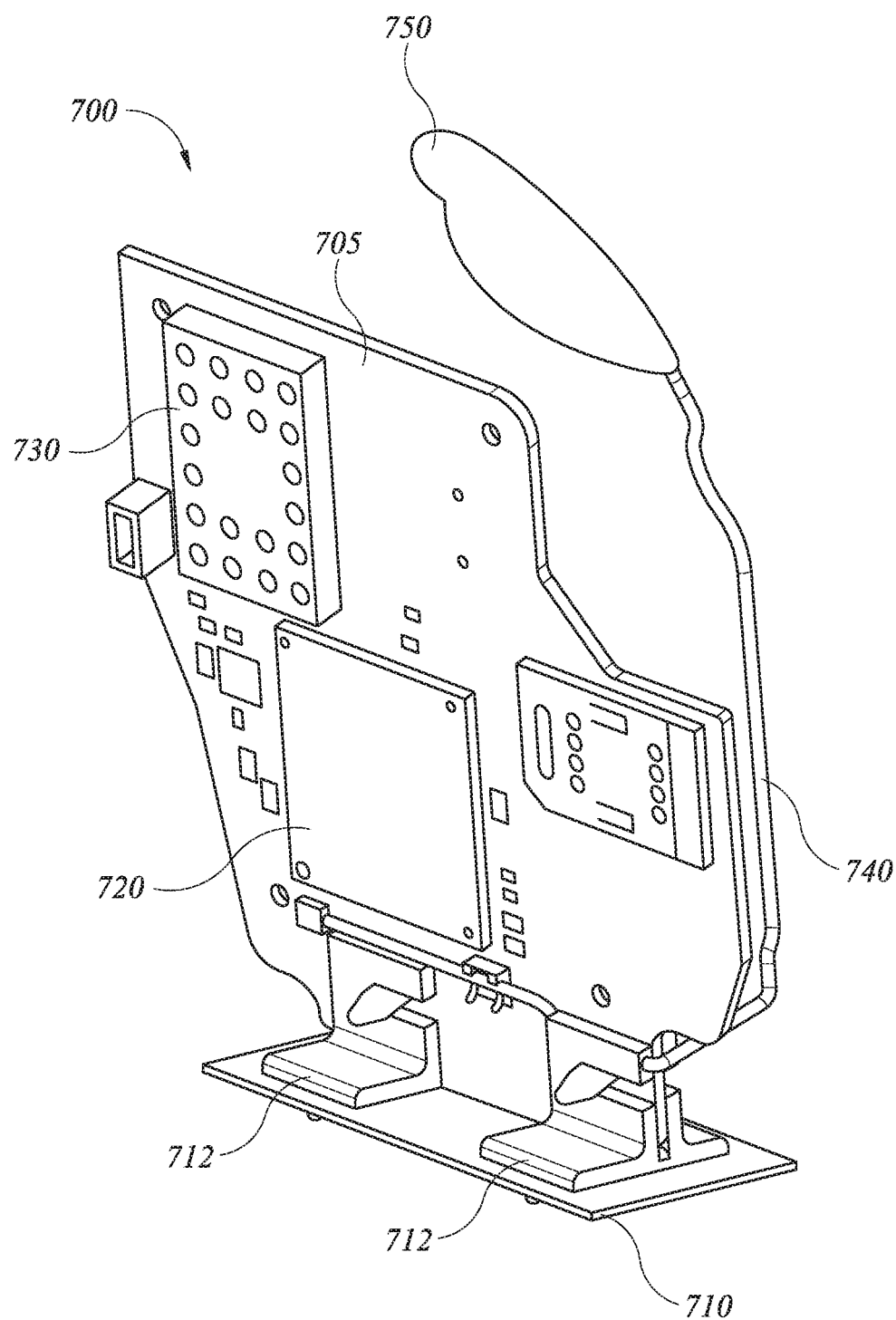
FIGS. 6A-6C illustrate a communications circuit board assembly, according to some embodiments.
Figure 6B:
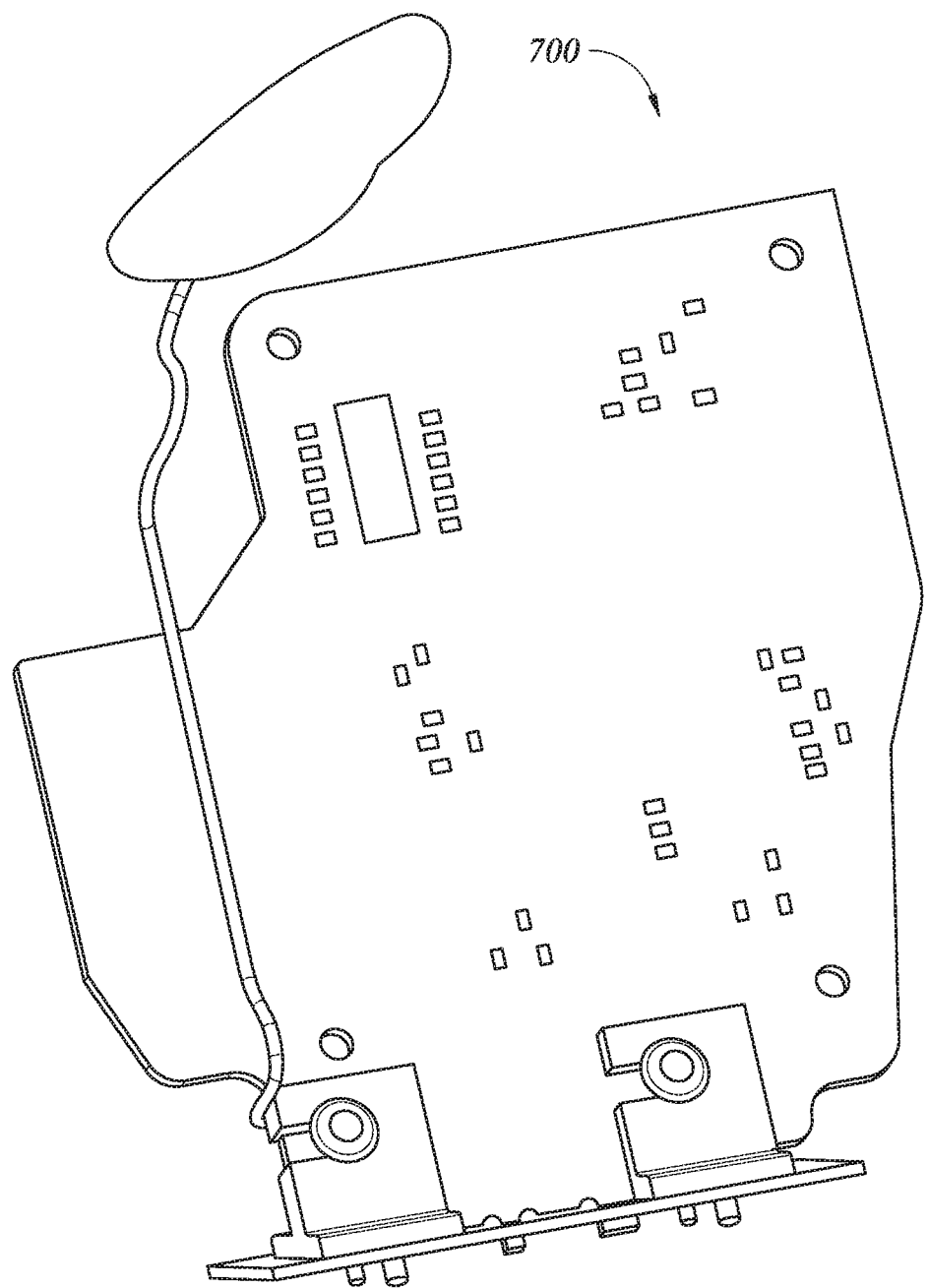

FIGS. 6A and 6B illustrate a front and back of a wireless communication PCB assembly 700 of a pump assembly, such as the pump assembly 230, according to some embodiments. The wireless communication PCB 700 assembly can, for example, be an embodiment of the communications circuit board assembly 411. The wireless communication PCB assembly 700 can include an antenna board 710 (such as PCB) and a processor or communications board PCB 705 with a shielded wireless communication controller 720, and a shielded voltage regulator 730. The antenna board 710 can be wireless mobile communications antenna, such a single-, dual-, tri-, quad- or the like band antenna for communicating via 2G, 3G, LTE, 4G, or the like. The antenna can be mounted to the communications PCB 705 with mounting brackets 712. The wireless communication PCB assembly 700 can be electrically coupled via a path 740 to a GPS antenna 750, which can be an embodiment of the GPS antenna 402.

Figure 6C:
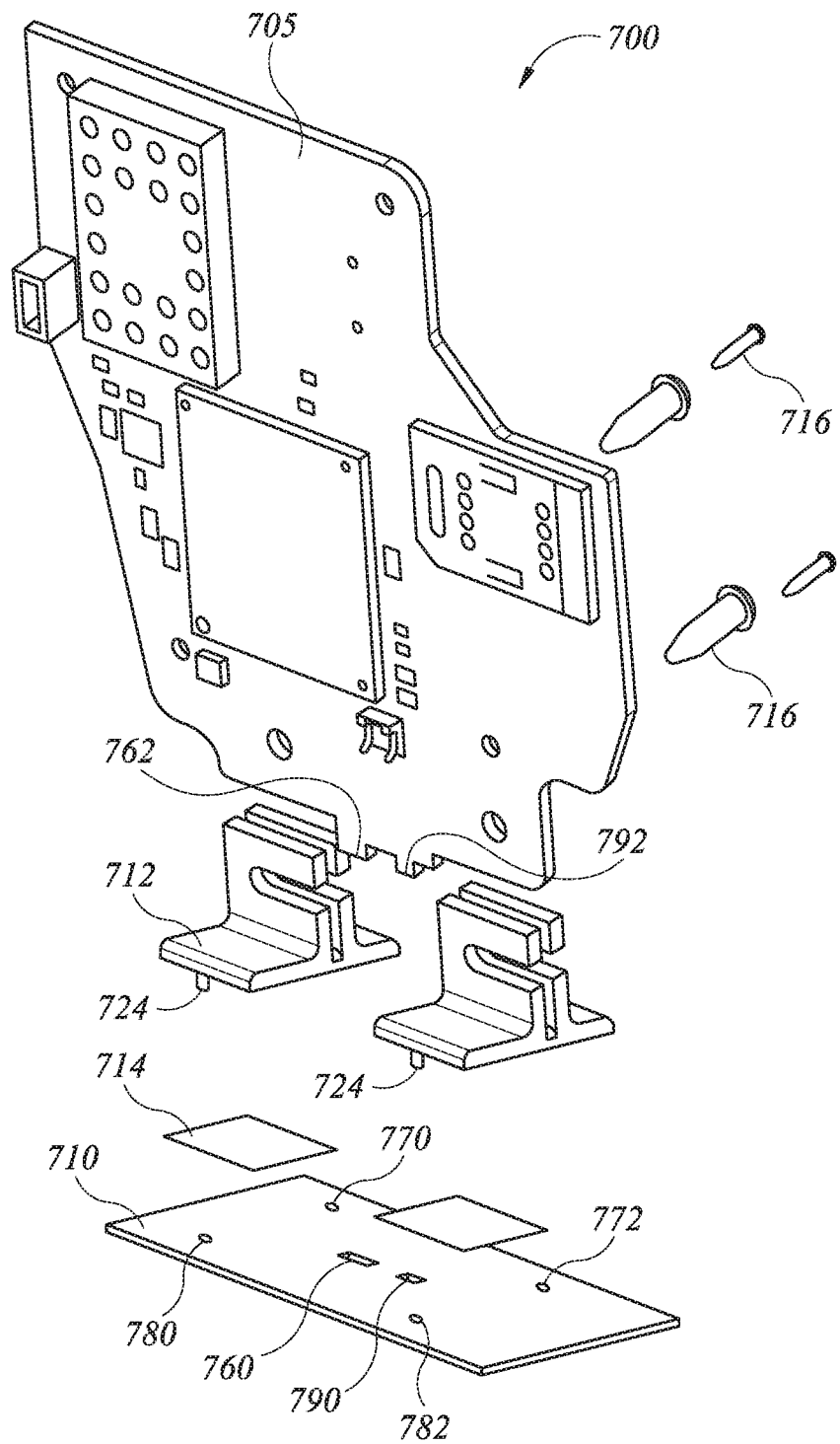

FIG. 6C illustrates a perspective view of components of the wireless communication PCB assembly 700 according to some embodiments. The antenna board 710 can be mounted to the communications PCB 705 with the mounting brackets 712 secured to the PCB 705 with pins, screws, or rivets 716. Although two brackets 712 are illustrated, in some embodiments one bracket or more than two brackets can be used. The brackets 712 can be secured to the antenna board 710 using tape 714 alone or in combination with pegs or pins 724 being aligned with (and when assembled fitting through) the holes 770, 772, 780, and 782 of the antenna board 710. Pegs or protrusions 762 and 792 of the PCB 705 also can be aligned with (and when assembled fit through) the holes 760 and 790 of the antenna board 710. The antenna can be oriented at any desired angle to the PCB 705, such as at 90 degrees, 80 degrees, 70 degrees, 60 degrees, and so on. In some implementations, desired orientation can be achieved by rotating or pivoting the brackets 712 about the rivets 716.

Figure 7A:
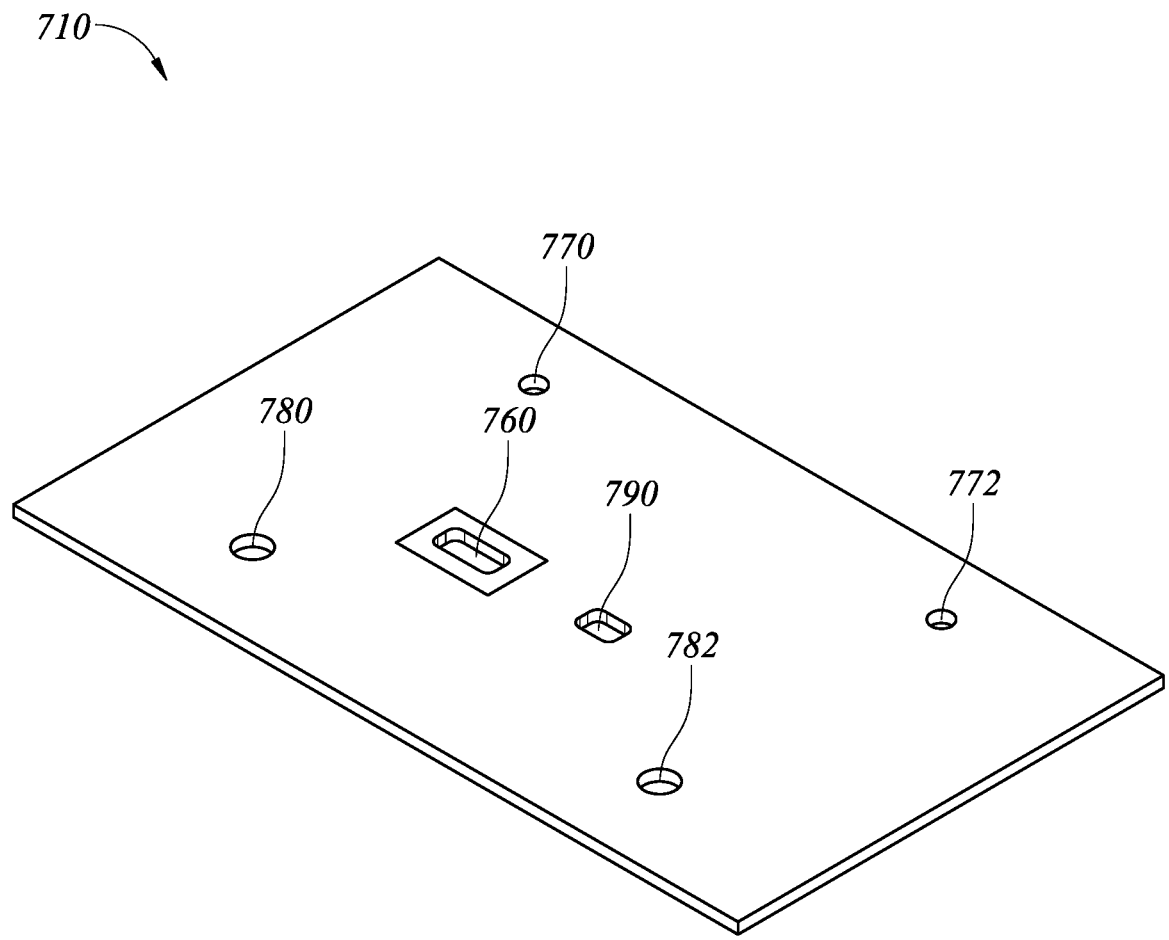
FIGS. 7A-7C illustrate communications antenna board according to some embodiments.
Figure 7B:
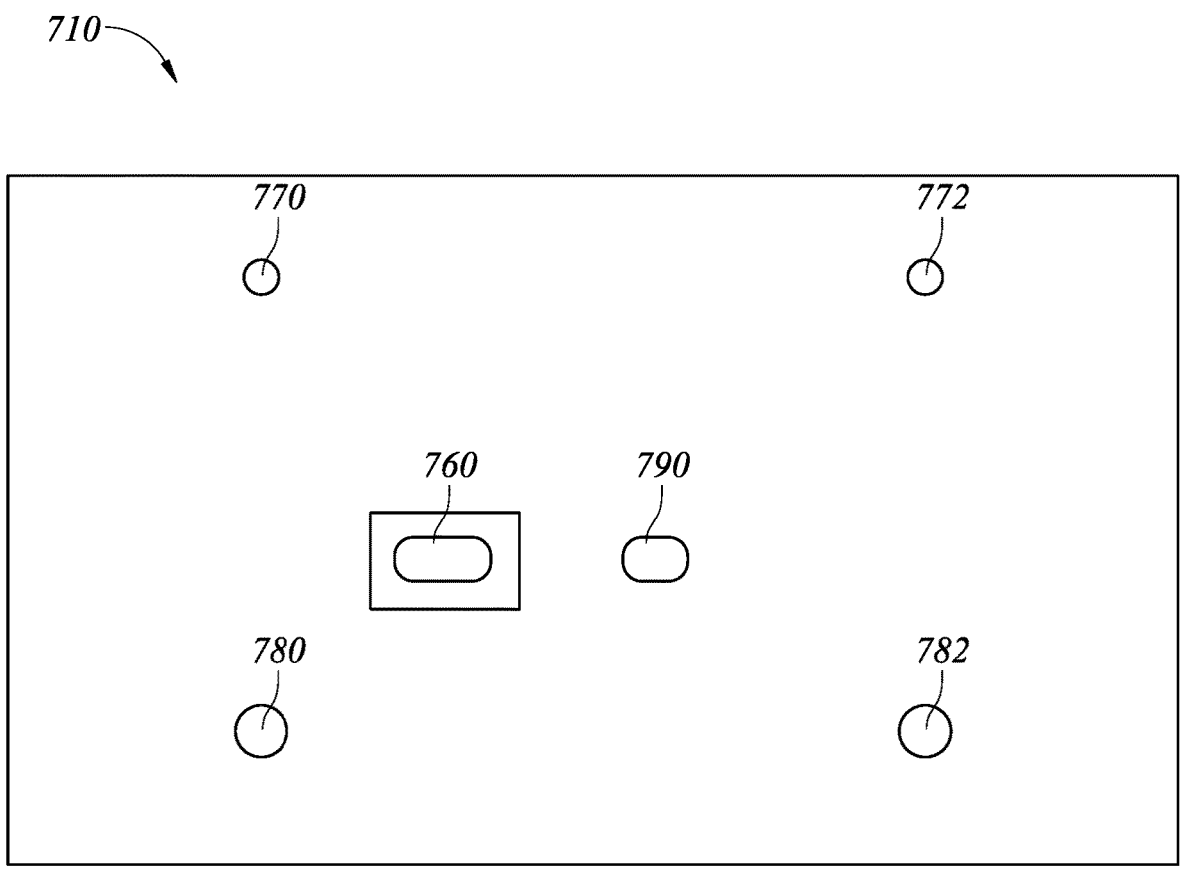
Figure 7C:
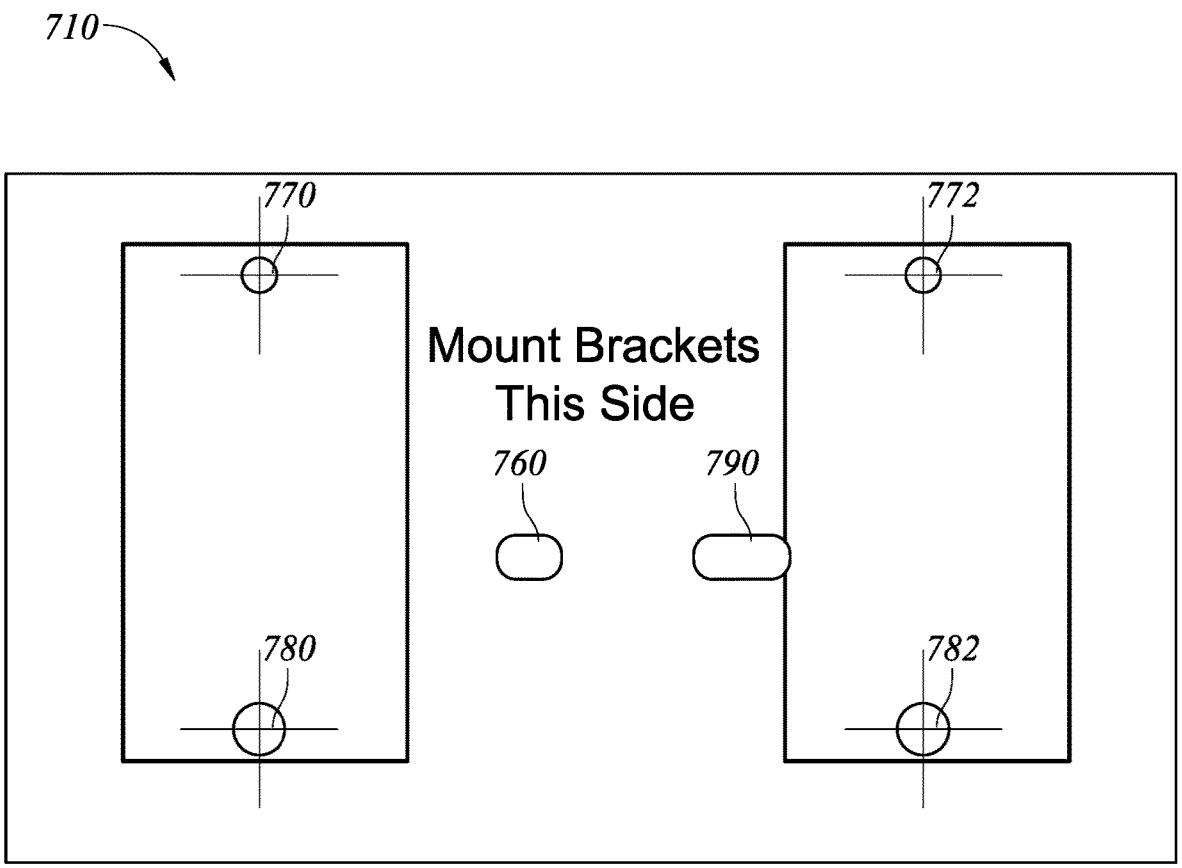

FIGS. 7A-7C illustrate a communications antenna, such as the antenna board 710, according to some embodiments. FIG. 7A shows the perspective view of the board 710 illustrating holes 770, 772, 780, and 782 for aligning and attaching the mounting brackets and holes 760 and 790 for aligning and attaching the protrusions 762 and 792 of the communications PCB 705. As described herein, the hole 760 also includes a signal connector or connection between the antenna and a controller, such as the communications controller 720. FIGS. 7B and 7C illustrate the top and bottom sides, respectively, of the antenna board 710. As is illustrated in FIG. 7C, the mounting brackets 712 are attached to the bottom side of the antenna board 710, which results in the top side of the antenna board 710 facing downward and away from the PCB 705 when the antenna board is attached or mounted to the PCB 705. In some embodiments, the mounting brackets 712 are attached to the top side of the antenna board 710.

Figure 8A:
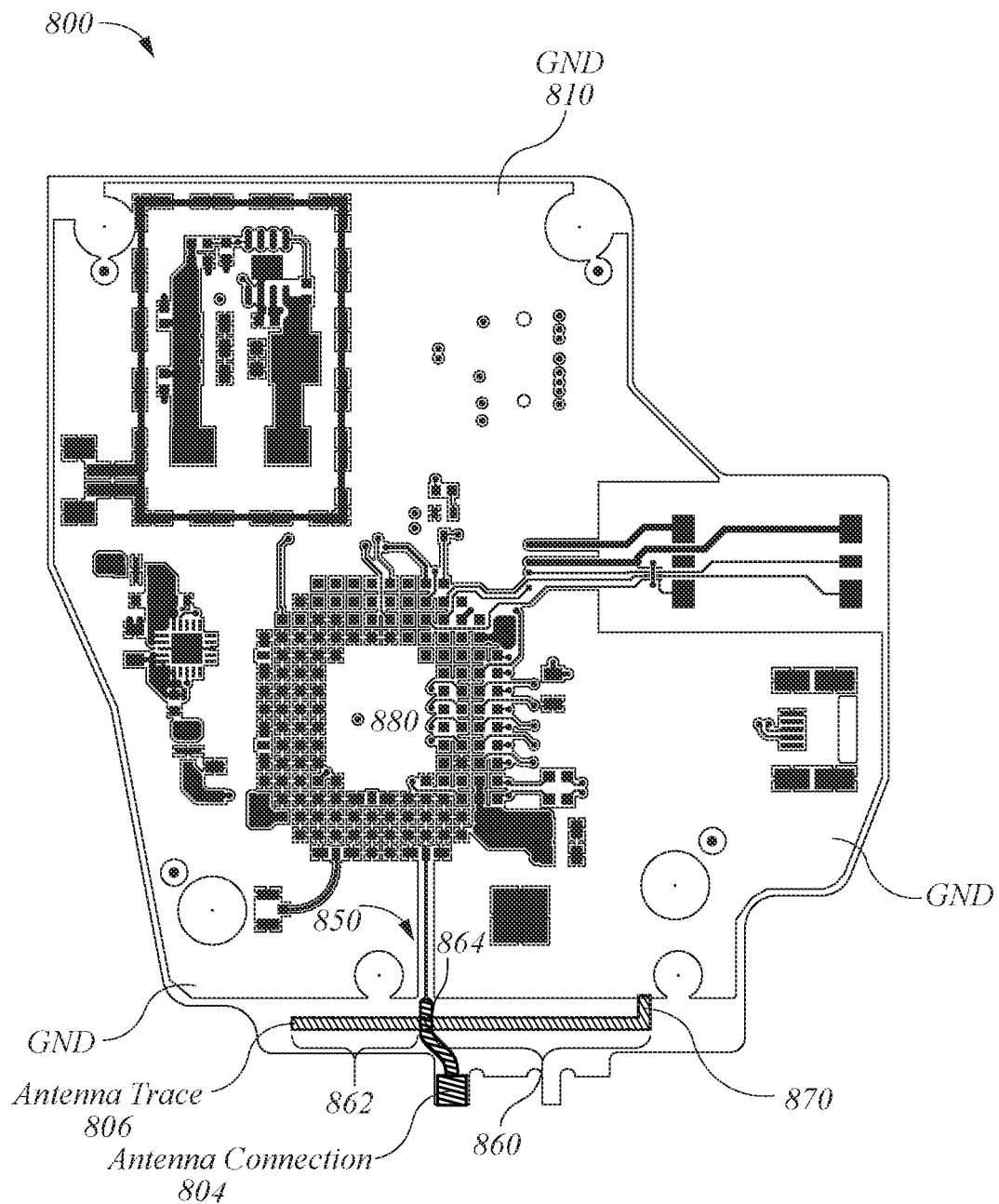
FIGS. 8A and 8B illustrate a top layer and bottom layer of a communications circuit board assembly, according to some embodiments.

FIG. 8A illustrates a top layer 800 of a wireless communication PCB assembly, such as the wireless PCB 705, according to some embodiments. In some embodiments, the top layer 800 can be a top film layer. The top layer 800 includes conductive portions (shown as darkened or shaded areas) and nonconductive portions or voids (shown as undarkened or white areas). The top layer 800 moreover includes multiple features including at least ground (GND) plane 810, a connector or connection 804 between the antenna board 710 and the PCB 705. The connection 804 can provide a transmit signal feed from a controller (for example, the communication controller 720) and the antenna board 710 when antenna is transmitting (or is in a transmit mode). Connection 804 can provide a receive signal feed from the antenna board 710 to the controller when the antenna is receiving (or is in a receive mode). The antenna connection 804 can, in some implementations, be the sole connection point for transmitting and receiving signals via the antenna board 710. Antenna trace 806, which includes first and second portions 860 and 862, is connected to the ground plane 810 at or near location 870. Location 870 can serve as shunt or ground connection of the antenna. The trace 806 includes conductive material, such as copper, and can serve as a ground trace or ground plane for the antenna board 710. Connection between the trace 806 and the ground plane 810 of the PCB 705 can be accomplished with a shunt or another suitable component. Antenna trace 806 can be connected to the communications controller (located in area 880) via a feed path 850. In certain implementations, the top side of the antenna board 710 (FIG. 7B) is placed facing down toward the ground and facing away from the PCB 705 when the antenna board is mounted to the PCB 705. Connection 760 can be located on the bottom side of the antenna board (FIG. 7C), which faces the PCB 705 when the antenna board is mounted to the PCB 705. In this configuration, connection 804 on the PCB 705 faces connection 760 on the antenna board 710. As is explained herein, protrusion 762 of the PCB 705 can be placed in the hole 760 of the antenna board 710. Electrical connection between connection 804 and 760 can be made, for example, using soldering or another suitable mechanism.

Figure 8B:
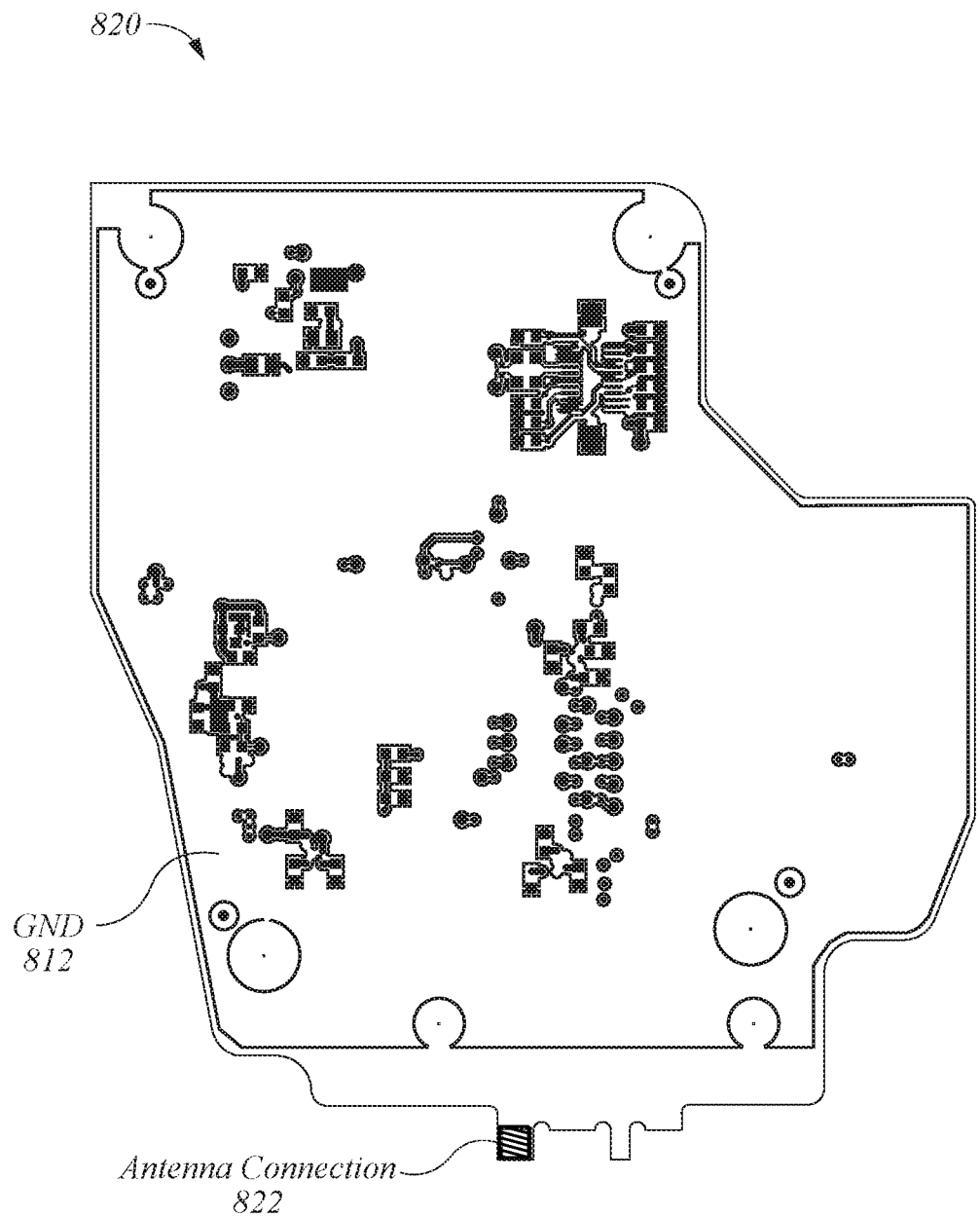

FIG. 8B illustrates a bottom layer 820 of the wireless communication PCB assembly of FIG. 8A according to some embodiments. In some embodiments, the bottom layer 820 can be a bottom film layer. The bottom layer 820 includes conductive portions (shown as darkened or shaded areas) and nonconductive portions or voids (shown as undarkened or white areas). The bottom layer 820 includes multiple features, such as at least a ground (GND) plane 812 and an antenna connector or connection 822. Connection 822 can be used as a mechanical connection for securing the antenna board 710. For instance, when the antenna board is positioned top side facing downward as explained herein, because connection 822 is positioned on the opposite side of the board with respect to connection 804, more reliable or secure mechanical connection can be made by soldering, gluing, or using another suitable attachment a portion of the top surface of the antenna board (for example, area on the top side including and/or surrounding the hole 760) to the connection 822. In such instances, connection 822 does not provide any electrical connectivity, but is used solely for mechanical support. As explained herein, protrusion 762 of the PCB 705 can be placed in the hole 760 of the antenna board 710 so that connection 822 is located proximal the top surface of the antenna board. Soldering the antenna board connection 760 on the opposite, bottom side of the antenna board 710 to the connection 804 can provide electrical connection and, optionally, additional mechanical support. In some embodiments, the locations of the antenna connection 822 and the connection 804 can be switched (for example, the antenna connection 822 can be placed on the top layer 800) particularly when the antenna board is positioned top side facing upward away from the ground.

Device Antenna

As described herein, the antenna can be a wireless antenna, such as a 2G, 3G, LT, 4G, or the like antenna. The antenna can be single-, dual-, tri-, quad-band and the like. For example, the antenna can be a dual-band 3G cellular antenna that transmits and receives electromagnetic signals in a low band (for example, 800 MHz band in North America, which can encompass 824 to 849 MHz and 869 to 894 MHz frequency ranges) and a high band (for example, 1800 MHz or 1900 MHz band in North America, which can encompass 1700 to 2100 MHz frequency range). The antenna can in addition or alternatively transmit and receive electromagnetic signals in low and high bands used in other regions, such as in Europe, which uses 900 MHz low band range and 1800 MHz high band range. The antenna can be a quad-band 3G antenna covering low and high bands for North America and Europe. In certain implementations, the antenna can transmit and receive at one or more additional or alternative frequencies or frequency ranges. The antenna can be an omnidirectional antenna. In certain cases, the antenna can be a directional antenna.

Figure 9A:
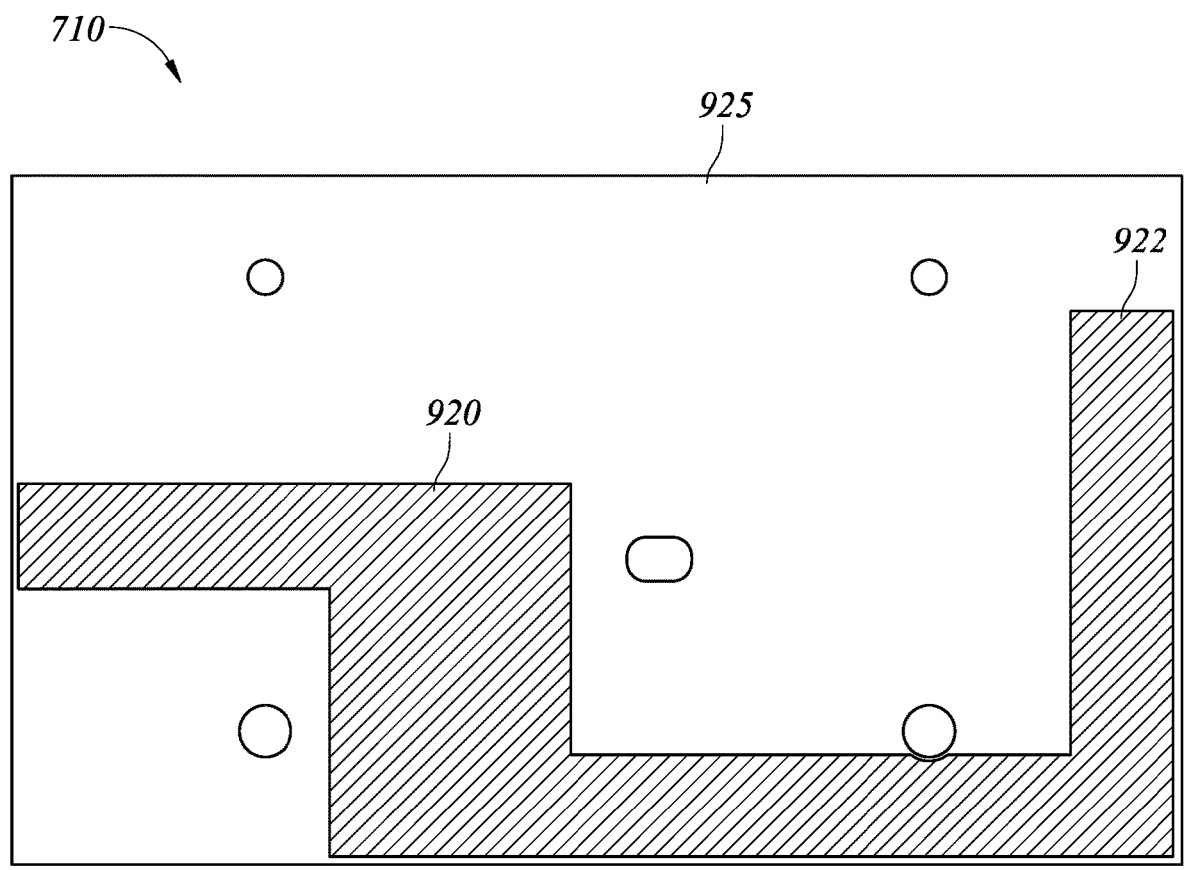
FIGS. 9A and 9B illustrate top layer and bottom layer of an antenna board according to some embodiments.
Figure 9B:
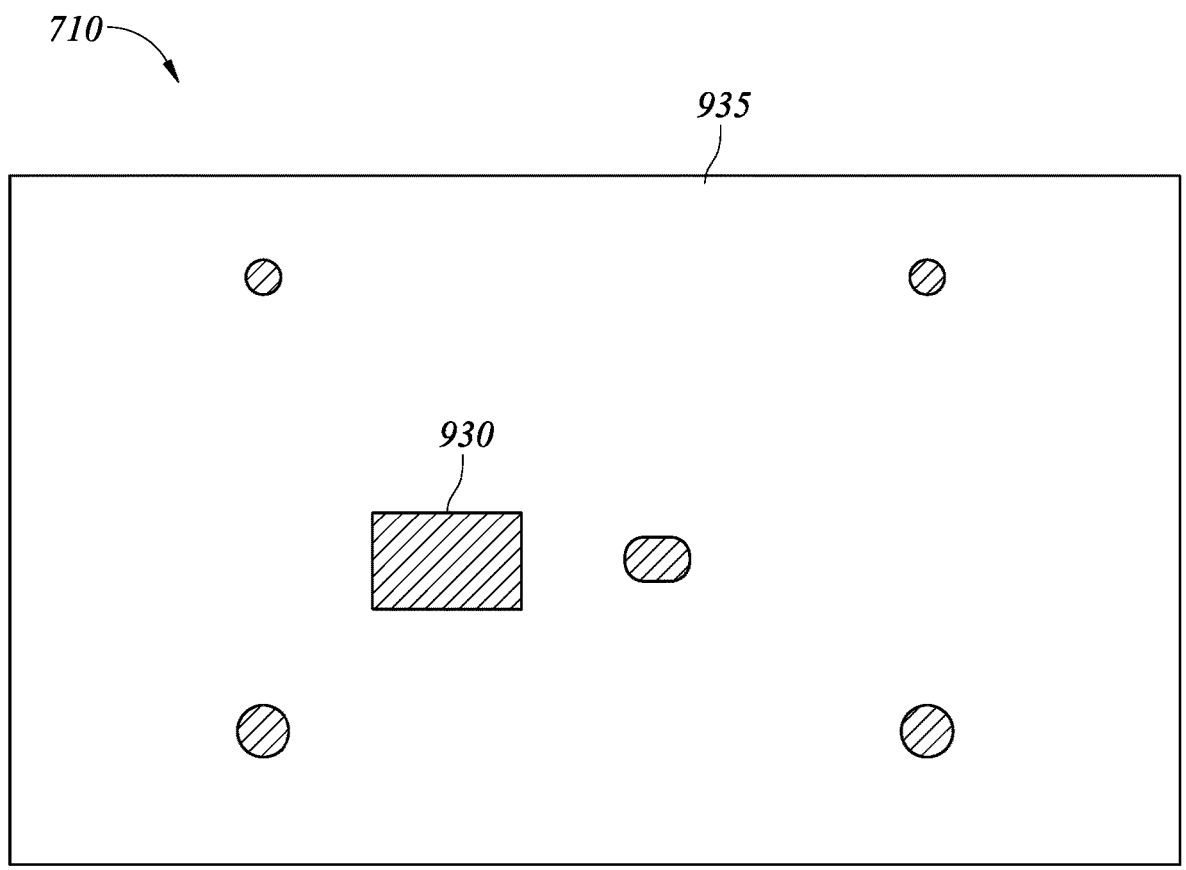

FIGS. 9A and 9B respectively illustrate front or top layer and back or bottom layer of an antenna board, such as the antenna board 710, according to some embodiments. The antenna board can be a PCB. Areas 925 and 935 illustrate non-conductive portions of the antenna board. Areas 920 and 922 illustrate conductive portions of the antenna board and correspond to the antenna. Conductive portions can be made out of copper or another conductive material. In some embodiments, areas 920 and 922 correspond to a trace on the antenna board. Such antenna can be referred to as a PCB antenna or a microstrip antenna. In certain implementations, the antenna can be a wire antenna, chip antenna, or the like.

The illustrated antenna can be a dual-band or quad-band cellular antenna, such as 3G antenna. The left trace 920 can represent high band portion that transmits and receives signals in the high band. The right trace 922 can represent low band portion that transmits and receives signals in the low band. In some instances, because high band range has wider bandwidth than low band range, the left trace 920 has more surface area (for example, is longer or wider) than the right trace 922.

In some embodiments, the antenna can be an inverted-F antenna, such as a planar inverted-F antenna (PIFA). Such antenna can be printed on a PCB using microstrip format, and accordingly can be compact and inexpensive to manufacture. The antenna can be a quarter-wave length antenna. In certain implementations the antenna can be a monopole antenna, patch antenna, inverted-L antenna, or another suitable type of antenna.

As is illustrated in FIG. 9B, the bottom layer of the antenna board includes a feed or connector 930, which is electrically connected to areas 920 and 922 on the top layer, which is opposite to the bottom layer. The connector 930 can correspond to the connector 760 described herein. As explained, when the antenna is mounted to a processor or communications board, such as the PCB 705, the bottom layer of the antenna can be positioned facing the PCB 705, and connector 930 can be connected to connection 804 (FIG. 8A) of the communications board. The top side of the antenna board with areas 920 and 922 can be positioned facing down toward the ground, and the antenna will transmit or radiate signals downward (and receive signals from below).

Connection 804 can be a mixed signal connection in which feed signal (coming from the communications controller to the antenna in the transmit mode and in the other direction in the receive mode) and ground connections are combined. In some embodiments, providing a path for the current to ground shifts the resonant frequency or frequency range of the antenna. Connection 804 can be the only connector for signals that are feed into or received from the antenna. As is illustrated in FIG. 8A, the feed signal from the communications controller can be delivered to the connection 804 via path or trace 850. In turn, the feed signal is delivered to the antenna via the connection between the connection 804 and the connector 930.

As is illustrated in FIG. 8A, in some implementations, the ground signal path, trace, or plane of the antenna is located on the processor or communications board (such as, the PCB 705) rather than on the antenna board. Such separation of the ground plane of the antenna, which is made up of traces 860 and 862, from the antenna board can be advantageous for optimizing performance of the antenna, including one or more of impedance or radiation, in one or more frequency bands of interest. As explained below, the length of traces 860 and 862 (measured from the intersection with the feed path 850) can be important to the performance of the antenna. Moving the ground plane to the PCB 705 can simplify the antenna design and obviate the need to have a hole in the antenna board to optimize the performance of the antenna. Such hole, for example, may be used for connecting the feed to the ground plane of the antenna board, which may be positioned on the opposite side of the antenna board (for instance, on the back side). Also, the design can be simplified by having a single connection point for the antenna, which is between the connection 804 and the connector 930. In such implementations, there is only one electrical connection that needs to be made (such as, soldered) during assembly. In some embodiments, the ground plane of the antenna can be positioned on the antenna board.

In some embodiments, the length of the traces 860 and 862 as measured from a feed point 864 where the feed path 850 intersects the antenna trace 806. The length of trace 860 or a gap can be selected to optimize one or more of impedance or radiation of the antenna in one or more frequency bands of interest. For example, the gap can be important for gamma matching, which may relate to optimizing the transmission and reception bandwidth of the antenna by moving the feed point (for example, 864) along the length of the antenna and with the antenna short-circuited at the previous feed location. Gamma matching can increase the real part of input impedance of the antenna. This technique can apply to an inverted-F antenna. Characteristics of the trace 860, such as the length, can be selected or adjusted to control the bandwidths in one or more bands, such as the high band or the low band. The length of the trace 862 can be selected to optimize performance in the high band (or another band of interest). For example, the length of trace 862 can optimize one or more of impedance or radiation of the antenna in the high band, provide wider bandwidth, or the like.

In some implementations, trace 806 can amplify the signal transmitted or received by the antenna. For example, this can be accomplished via reflecting fringing fields radiated by the antenna.

In some embodiments, a pump assembly, such as the pump assembly 230, can communicate using an antenna, such as the antenna board 710, with one or more other electronic devices. The antenna can be positioned near a base of the pump assembly or near a canister coupled to the pump assembly. The position of the antenna proximate the canister can enable the canister to function as an electromagnetic shield or insulator from EMI, ESD, or electric shock (such as from a defibrillator) and protect the antenna from ESD and internal noise from other electronic components of the pump assembly. Such positioning may also desirably afford additional space for increasing a size of the antenna to improve a signal strength obtained with the antenna, as well as to enable the canister to function as a spacer to space the antenna from the ground or other surface on which the pump assembly is positioned.

The antenna can be oriented to face downward (for example, toward the ground, floor, desk, bed, or other surface on which the pump assembly is positioned) rather than upward (for example, toward a ceiling or sky) or sideward (for example, toward side wall of a room) when the pump assembly is oriented for delivery of negative pressure therapy. This orientation can allow the antenna to reflect a communication signal (for example, a strongest signal or most of the energy of the signal received or output by the antenna) off the ground or another surface on which the pump assembly is positioned.

In some implementations, the antenna can be positioned as far as possible from a ground plane or another plane of the PCB 705 to which it is connected. The antenna however can still be positioned inside the pump assembly housing to prevent the antenna from picking up undesirable PCB noise or being shielded by the PCB or other board components.

Other Variations

In one embodiment, an apparatus for applying negative pressure to a wound is disclosed. The apparatus can include a housing, a negative pressure source, a canister, a user interface, and one or more controllers. The negative pressure source can provide negative pressure via a fluid flow path to a wound dressing. The canister can be positioned in the fluid flow path and collect fluid removed from the wound dressing. The one or more controllers can: activate and deactivate the negative pressure source, and output an alarm indicating presence of a leak in the fluid flow path or that pressure in the fluid flow path failed to satisfy a desired pressure threshold. The one or more controllers can continue to activate and deactivate the negative pressure source subsequent to the wound dressing being exposed to a defibrillation shock while the negative pressure source is maintaining negative pressure below a negative pressure threshold, or the one or more controllers may not erroneously output the alarm as a result of the wound dressing being exposed to a defibrillation shock while the negative pressure source is maintaining negative pressure below the negative pressure threshold. The apparatus can be performing negative pressure therapy when the magnitude is maintained below the negative pressure threshold. The apparatus, moreover can function correctly and safely after a monophasic or biphasic electrical pulse of 5 KV/250 J (or another suitable intensity) from an external defibrillator.

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value. Moreover, although blocks of the various processes may be described in terms of determining whether a value meets or does not meet a particular threshold, the blocks can be similarly understood, for example, in terms of a value (i) being below or above a threshold or (ii) satisfying or not satisfying a threshold.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

User interface screens illustrated and described herein can include additional or alternative components. These components can include menus, lists, buttons, text boxes, labels, radio buttons, scroll bars, sliders, checkboxes, combo boxes, status bars, dialog boxes, windows, and the like. User interface screens can include additional or alternative information. Components can be arranged, grouped, displayed in any suitable order.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. An apparatus for applying negative pressure to a wound, the apparatus comprising:
    a housing;
    a negative pressure source positioned within the housing and configured to provide negative pressure via a fluid flow path to a wound covered by a wound dressing, the negative pressure source being further configured to provide negative pressure in accordance with a set of negative pressure wound therapy parameters comprising a negative pressure set point;
    an electronic control circuitry positioned within the housing and configured to cause the negative pressure source to provide negative pressure to the wound at the negative pressure set point;
    a communications board positioned within the housing and being controlled by the electronic control circuitry, the communications board comprising a ground area located on the communications board, and the communications board including a controller and a conductive trace, the controller being configured to transmit first data comprising at least one of a location of the housing, logs corresponding to provision of negative pressure, or alarms caused by provision of negative pressure and receive second data comprising at least one of data for tracking the location of the housing, data for adjusting the set of negative pressure wound therapy parameters, or data for upgrading software or firmware, and the conductive trace being electrically connected to the ground area and the controller; and
    an antenna board positioned within the housing and mechanically mounted to the communications board, the antenna board being electrically connected to the communications board via no more than a single electrical connector positioned on the communications board, the antenna board including a conductive area located on a side of the antenna board, and the conductive area being electrically coupled to the controller via the single electrical connector and the conductive trace and configured to radiate electromagnetic waves, wherein the conductive area, the conductive trace, and the ground area together form an antenna configured to wirelessly transmit the first data and receive the second data.

2. The apparatus of claim 1, wherein the conductive area comprises another conductive trace, and the ground area comprises a ground plane.

3. The apparatus of claim 2, wherein the ground plane is electrically connected to the conductive trace via a shunt.

4. The apparatus of claim 1, wherein:
the conductive trace is electrically connected to the controller via a feed;
the conductive trace is divided by the feed into a first portion and a second portion; and
the first portion is electrically connected to the ground area, a length of the first portion optimizing transmission and reception by the antenna of the signals in a first frequency band.

5. The apparatus of claim 4, wherein a length of the second portion optimizes transmission and reception by the antenna of the signals in a second frequency band different from the first frequency band.

6. The apparatus of claim 2, wherein the another conductive trace comprises first and second conductive trace portions configured to receive and transmit signals in high and low frequency bands.

7. The apparatus of claim 6, wherein the first conductive trace portion is associated with the high frequency band and has a greater surface area than the second conductive trace portion that is associated with the low frequency band.

8. The apparatus of claim 1, wherein the single electrical connector comprises a protrusion electrically connected to the antenna board via a hole in the antenna board.

9. The apparatus of claim 1, wherein the single electrical connector provides a connection for signal feed and ground.

10. The apparatus of claim 1, wherein the antenna board is a printed circuit board.

11. The apparatus of claim 1, wherein the antenna is a planar inverted F-antenna.

12. The apparatus of claim 1, wherein the antenna is a dual-band cellular antenna.

13. The apparatus of claim 1, wherein the antenna board is positioned so that the conductive area faces away from the communications board.

14. The apparatus of claim 13, further comprising a canister configured to store at least some fluid removed from the wound, wherein the antenna board is positioned so that the conductive area faces the canister.

15. The apparatus of claim 9, wherein the single electrical connector comprises a signal feed connection on a first side and a ground connection on a second side opposite the first side.

16. The apparatus of claim 1, wherein the communications board comprises a printed circuit board.

17. The apparatus of claim 8, wherein the conductive area is located on a first side of the antenna board, and wherein the hole in the antenna board comprises an electrical connector located on a second side of the antenna board opposite the first side.

18. The apparatus of claim 8, wherein the protrusion comprises a first side and a second side opposite the first side, the first and second sides being soldered to the hole in the antenna board, the first side providing an electrical connection to the antenna board, and the second side providing a mechanical connection but not the electrical connection.

19. The apparatus of claim 1, wherein the antenna is configured to wirelessly transmit and receive signals in a 4G frequency band.

20. The apparatus of claim 1, wherein the antenna board is mounted perpendicular to the communications board, and wherein the antenna is configured to radiate electromagnetic waves toward a surface on which the housing is positioned.

* * * * *

UNITED STATES PATENT AND TRADEMARK OFFICE
CERTIFICATE OF CORRECTION

Page 1 of 1

PATENT NO. : 11,974,903 B2
APPLICATION NO. : 16/491542
DATED : May 7, 2024
INVENTOR(S) : Manveer Brar It is certified that error appears in the above-identified patent and that said Letters Patent is hereby corrected as shown below:

In the Claims

Column 17, Line 17, Claim 4, delete "of the" and insert -- of --.

Column 17, Line 21, Claim 5, delete "of the" and insert -- of --.

Signed and Sealed this
Twenty-third Day of July, 2024

Katherine Kelly Vidal
*Director of the United States Patent and Trademark Office*